US012035999B2

(12) United States Patent　　(10) Patent No.: US 12,035,999 B2
Ito et al.　　(45) Date of Patent:　　Jul. 16, 2024

(54) ENDOSCOPE APPARATUS, PROCESSING DEVICE AND PROCESSING METHOD

(71) Applicant: OLYMPUS CORPORATION, Tokyo (JP)

(72) Inventors: Takeshi Ito, Hino (JP); Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 690 days.

(21) Appl. No.: 17/133,754

(22) Filed: Dec. 24, 2020

(65) Prior Publication Data

US 2021/0113075 A1　　Apr. 22, 2021

Related U.S. Application Data

(63) Continuation of application No. PCT/JP2018/026075, filed on Jul. 10, 2018.

(51) Int. Cl.
*A61B 1/00*　　(2006.01)
*A61B 1/04*　　(2006.01)
(Continued)

(52) U.S. Cl.
CPC ...... *A61B 5/0086* (2013.01); *A61B 1/000094* (2022.02); *A61B 1/0005* (2013.01);
(Continued)

(58) Field of Classification Search
CPC . A61B 1/000094; A61B 1/046; A61B 1/0005; A61B 1/00186; A61B 1/0638; A61B 1/000096; H04N 25/134
See application file for complete search history.

(56) References Cited

U.S. PATENT DOCUMENTS

2006/0211915 A1* 9/2006 Takeuchi ................. A61B 1/05
　　　　　　　　　　　　　　　　　　600/109
2008/0017787 A1 　 1/2008 Okawa et al.
(Continued)

FOREIGN PATENT DOCUMENTS

JP　　2006-198032 A　　8/2006
JP　　2010-172673 A　　8/2010
(Continued)

OTHER PUBLICATIONS

International Search Report dated Oct. 9, 2018 issued in PCT/JP2018/026075, together with an English-language translation.

*Primary Examiner* — Timothy J Neal
(74) *Attorney, Agent, or Firm* — Scully, Scott, Murphy & Presser, P.C.

(57) ABSTRACT

An endoscope apparatus includes: an imaging device; a light source device; a first processing circuit; and a second processing circuit. The light source device can emit first light and fourth light having peak wavelengths in a transmission wavelength band of the blue color filter, second light, and third light and fifth light having peak wavelengths in a transmission wavelength band of the red color filter. The light source device emits the third light in a first imaging frame and the fifth light in a second imaging frame. The first processing circuit generates a display image based on any one of a first image group including images corresponding to the third light and the fifth light and a second image group including an image corresponding to the fourth light, and outputs a remaining one of the first image group and the second image group to the second processing circuit.

9 Claims, 8 Drawing Sheets

(51) Int. Cl.
    *A61B 1/06*          (2006.01)
    *A61B 5/00*          (2006.01)
    *H04N 25/13*        (2023.01)

(52) U.S. Cl.
    CPC .......... *A61B 1/00186* (2013.01); *A61B 1/046* (2022.02); *A61B 1/0638* (2013.01); *H04N 25/134* (2023.01); *A61B 1/000096* (2022.02); *A61B 1/043* (2013.01); *A61B 1/063* (2013.01)

(56)             References Cited

U.S. PATENT DOCUMENTS

| | | | |
|---|---|---|---|
| 2011/0028790 A1* | 2/2011 | Farr | A61B 1/0676 600/187 |
| 2011/0245642 A1* | 10/2011 | Minetoma | A61B 1/0655 600/324 |
| 2012/0190922 A1 | 7/2012 | Kaku | |
| 2017/0258296 A1* | 9/2017 | Kaku | A61B 1/044 |
| 2018/0218499 A1 | 8/2018 | Kamon | |

FOREIGN PATENT DOCUMENTS

| | | | |
|---|---|---|---|
| JP | 2012-152279 A | 8/2012 | |
| JP | 2016-144626 A | 8/2016 | |
| JP | 2018-38675 A | 3/2018 | |
| WO | 2005/104926 A1 | 11/2005 | |
| WO | 2017/057573 A1 | 4/2017 | |

\* cited by examiner

ENDOSCOPE APPARATUS, PROCESSING DEVICE AND PROCESSING METHOD

CROSS REFERENCE TO RELATED APPLICATION

This application is a continuation of International Patent Application No. PCT/JP2018/026075, having an international filing date of Jul. 10, 2018, which designated the United States, the entirety of which is incorporated herein by reference.

BACKGROUND

Endoscope apparatuses including a diagnosis support function are known. A proposed example of diagnosis support includes a function for extracting a lesion part from an image by artificial intelligence (AI) and presenting the lesion part. For example, JP-A-2016-144626 discloses an image processing device that is used for an endoscope apparatus, and calculates a diagnosis support parameter based on blood vessel information of an observation object. The image processing device disclosed in JP-A-2016-144626 extracts the blood vessel information from a special light image, and presents the special light image to an observer to support making a diagnosis. Furthermore, JP-A-2012-152279 discloses a method for performing the diagnosis support. The method includes performing matching between a blood vessel pattern acquired from a special light image and blood vessel patterns stored in advance, and performing the diagnosis support based on a result of the matching. When the result of the matching indicates a match, a message for requesting a change in a mode of imaging or observation is displayed.

SUMMARY

According to one aspect of the disclosure, there is provided an imaging device that includes an image sensor with blue, green, and red color filters, and captures an image of an object;
a light source device that emits a plurality of types of light with different colors as illumination light for the object;
a first processing circuit that generates an image based on an image signal from the imaging device; and
a second processing circuit that generates diagnosis support information based on the image input from the first processing circuit,
wherein the light source device is configured to emit
first light having a peak wavelength in a transmission wavelength band of the blue color filter,
second light having a peak wavelength in a transmission wavelength band of the green color filter,
third light having a peak wavelength in a transmission wavelength band of the red color filter,
fourth light having a peak wavelength in the transmission wavelength band of the blue color filter, and
fifth light having a peak wavelength in the transmission wavelength band of the red color filter,
the light source device emits
the third light in a first imaging frame and
the fifth light in a second imaging frame before or after the first imaging frame, and
the first processing circuit
generates a display image based on any one of a first image group including at least images corresponding to the third light and the fifth light and a second image group including at least an image corresponding to the fourth light, and outputs a remaining one of the first image group and the second image group to the second processing circuit.

According to another aspect of the disclosure, there is provided an endoscope apparatus comprising:
an imaging device that captures an image of an object;
a light source device that emits first to m-th light with different colors as illumination light for the object, m being an integer of two or more; and
a first processing circuit that generates first to n-th images based on an image signal from the imaging device, n being an integer of two or more, the first to n-th images each corresponding to any one of the first to m-th light,
wherein the first processing circuit
generates a display image based on a display image group including some images of the first to n-th images, and outputs any one of a support image and a support image group to a second processing circuit, the support image being different from the display image, the support image group being at least partly different from the display image,
the second processing circuit
acquires diagnosis support information based on the one of the support image and the support image group acquired from the first processing circuit, and
the first processing circuit
performs image processing based on the diagnosis support information to the display image group, and outputs a resultant to a display.

According to another aspect of the disclosure, there is provided a processing device comprising:
a storage device that stores first to n-th images, n being an integer of two or more; and
a first processing circuit that acquires the first to n-th images from the storage device, the first to n-th images each corresponding to any one of first to m-th light with different colors, m being an integer of two or more,
wherein the first processing circuit
generates a display image based on a display image group including some images of the first to n-th images, and outputs any one of a support image and a support image group to a second processing circuit, the support image being different from the display image, the support image group being at least partly different from the display image,
the second processing circuit acquires diagnosis support information based on the one of the support image and the support image group, and
the first processing circuit
performs image processing based on the diagnosis support information to the display image group, and outputs a resultant to a display.

According to another aspect of the disclosure, there is provided a processing method comprising:
generating first to n-th images each corresponding to any one of first to m-th light with different colors by a first processing circuit, n being an integer of two or more, m being an integer of two or more;
generating a display image based on a display image group including some images of the first to n-th images by the first processing circuit;
outputting any one of a support image and a support image group to a second processing circuit by the first processing circuit, the support image being different from the display image, the support image group being at least partly different from the display image;
acquiring diagnosis support information based on the one of the support image and the support image group by the second processing circuit; and performing image processing based on the diagnosis support information to the display image group to output a resultant to a display by the first processing circuit.

DESCRIPTION OF EXEMPLARY EMBODIMENTS

Figure 1:
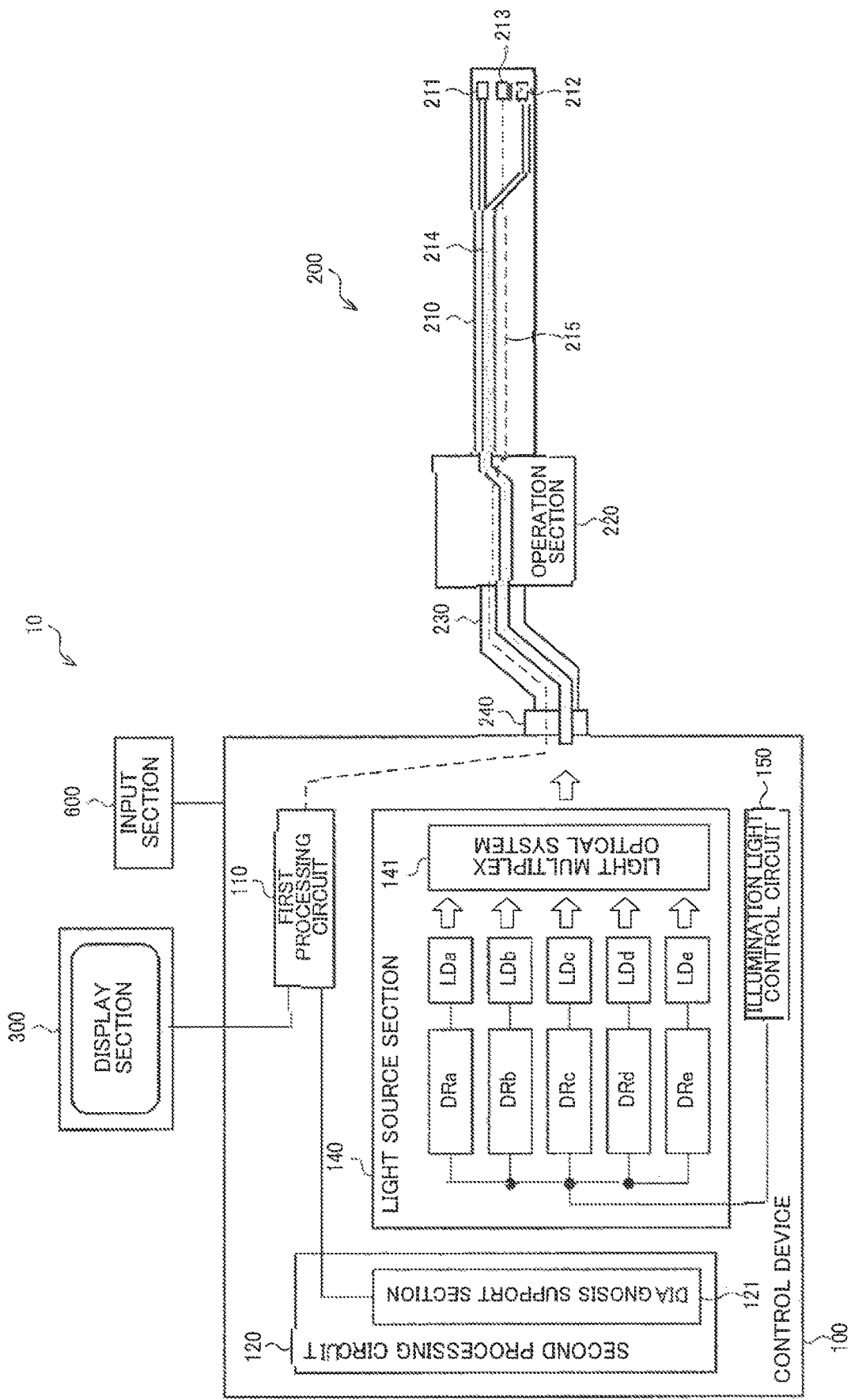
FIG. 1 is a first configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is a first configuration example of an endoscope apparatus 10. An example of the endoscope apparatus for medical use, such as for digestive organs, is described below, however, an applicable target of the present disclosure is not limited to this. That is, the endoscope apparatus as used in this specification means general equipment including an insertion section for observing insides of recessed portions of various observation targets. For example, the endoscope apparatus is an endoscope apparatus for medical use that is used for a medical examination of a living body, or an endoscope apparatus for industrial use.

The endoscope apparatus 10 in FIG. 1 includes a control device 100, a scope section 200, a display section 300, and an input section 600. The control device 100 is also referred to as a main body section. The scope section 200 is also referred to as a scope, an imaging section, or an imaging device. The display section 300 is also referred to as a display, or a display device. The input section 600 is also referred to as an input device, or an operation device.

First of all, a configuration of the endoscope apparatus 10 is described.

The scope section 200 includes an insertion section, 210, an operation section 220, a connecting cable 230, and a connector 240. The insertion section 210 has flexibility and can be inserted into a body cavity of a living body. The body cavity of the living body is an object in the present embodiment. The object is also referred to as an observation target or an observation object. The object is not illustrated in FIG. 1. An operator such as a physician or a surgeon holds and uses the operation section 220 to operate the endoscope apparatus 10. The connecting cable 230 connects the control device 100 and the scope section 200, and has flexibility. The connector 240 is disposed at an end of the connecting cable 230 to make the scope section 200 attachable to/detachable from the control device 100.

The insertion section 210 includes two illumination lenses 211 and 212 and an imaging unit 213 at an distal end. The illumination lenses 211 and 212 emit illumination light toward the object, and the imaging unit 213 captures an image by receiving the illumination light reflected or scattered from a surface of the object.

The scope section 200 includes a light guide path 214. The control device 100 includes a light source section 140. The light guide path 214 guides the illumination light emitted from the light source section 140 to the illumination lenses 211 and 212. The light guide path 214 is an optical fiber bundle extending from the connector 240 to the illumination lenses 211 and 212 via insides of the connecting cable 230 and the operation section 220. The light guide path 214 is bundled in a single bundle on a side of the connector 240 and is divided into two bundles in the insertion section 210 to be optically connected to the two illumination lenses 211 and 212.

The illumination lenses 211 and 212 spread the illumination light guided by the optical fiber bundle at a desired radiation angle. Each of the illumination lenses 211 and 212 is an illumination optical system including a single or a plurality of lenses.

The imaging unit 213 includes an imaging optical system and an image sensor. In the present embodiment, the image sensor is a CMOS imager including RGB color filters arranged in Bayer array. That is, the image sensor is an image sensor of a primary color filter type including an R pixel, a G pixel, and a B pixel.

The scope section 200 includes an image signal line 215 that transmits an image signal of an image captured by the imaging unit 213 to the control device 100. The image signal line 215 is disposed in the insertion section 210, the operation section 220, and the connecting cable 230, and is electrically connected to the control device 100 via the connector 240. The image signal line 215 may be any signal line as long as it can transmit the image signal. For example, the image signal line 215 is an electrical line or an optical fiber for optical communication. The image signal line 215 is illustrated by a single line in FIG. 1, however, a plurality of signal lines may be disposed according to a quantity of image signals or transmission speed.

The insertion section 210 according to the present embodiment may include various functions or mechanisms not illustrated. For example, the insertion section 210 may include a curving mechanism for curving a distal end portion, a forceps hole for inserting forceps or the like to perform various treatment, or an air and water supply pipe. The air and water supply pipe is a pipe for spouting or sucking liquid or gas.

The control device 100 includes the light source section 140 that emits the illumination light, a illumination light control circuit 150 that controls a quantity of light or emitting timing of the illumination light, or the like, a first processing circuit 110 that performs image processing to the image signal from the imaging unit 213, and a second processing circuit 120 that generates diagnosis support information based on an image output from the first processing circuit 110. The light source section 140 is also referred to as a light source device. The first processing circuit 110 is also referred to as an image processing circuit.

For example, the first processing circuit 110 and the second processing circuit 120 are implemented by separate integrated circuit devices. The first processing circuit 110 is, for example, a processor or an application specific integrated circuit (ASIC). The second processing circuit 120 is, for example, a processor or an ASIC. Alternatively, the first processing circuit 110 and the second processing circuit 120 may be integrated into a single integrated circuit device. Alternatively, the first processing circuit 110 may include a plurality of integrated circuit devices. For example, the first processing circuit 110 may include an image processing circuit that generates first to n-th images, and an image group output circuit that outputs a display image group and a support image group. At this time, the image processing circuit and the image group output circuit each may be configured as a separate circuit. For example, the image processing circuit and the image group output circuit each may be configured by an integrated circuit device.

The light source section 140 includes a plurality of light sources LDa to LDe, driving circuits DRa to DRe that drives the light sources LDa to LDe, and a light multiplex optical system 141 that multiplexes light emitted from the light sources LDa to LDe.

The light sources LDa to LDe are semiconductor laser elements (laser diodes). In this case, the illumination light is laser light. Alternatively, the light sources LDa to LDe may be light emitting diodes (LEDs). For example, LEDs that emit narrowband light having a wavelength band of about several tens of nm may be used. However, the illumination light is not limited to the narrowband light. It is possible to use illumination light having a band suitable for visibility of a display image or an extraction method of support information, for example. The following describes an example where the light sources LDa to LDe are semiconductor laser elements.

Figure 2:
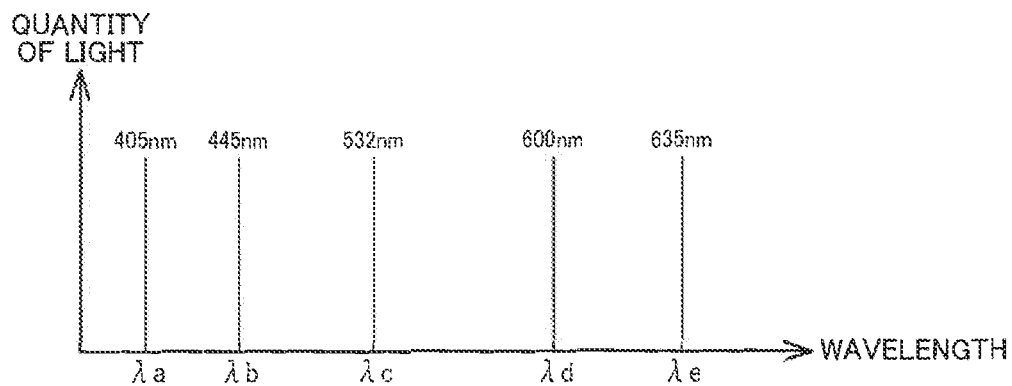
FIG. 2 is an example of laser light emitted by light sources in the first configuration example.

FIG. 2 is an example of laser light emitted by the light sources LDa to LDe. As illustrated in FIG. 2, the light source LDa emits blue-violet laser light having a wavelength $\lambda a=405$ nm. The light source LDb emits blue laser light having a wavelength $\lambda b=445$ nm. The light source LDc emits green laser light having a wavelength $\lambda c=532$ nm. The light source LDd emits orange laser light having a wavelength $\lambda d=600$ nm. The light source LDe emits red laser light having a wavelength $\lambda e=635$ nm. In FIG. 2, the quantities of light emitted by the respective light sources are almost the same, however, the quantities of light emitted by the light sources are not limited to these. For example, it is possible to adopt quantities of light suitable for the visibility of the display image or the extraction method of the support information.

The driving circuits DRa to DRe are electrically connected to the corresponding light sources LDa to LDe, respectively. That is, as illustrated in FIG. 1, the driving circuit DRa is electrically connected to the light source LDa, the driving circuit DRb to the light source LDb, the driving circuit DRc to the light source LDc, the driving circuit DRd to the light source LDd, and the driving circuit DRe to the light source LDe. The light sources LDa to LDe oscillate laser light by electricity supplied from the driving circuits DRa to DRe.

The driving circuits DRa to DRe are electrically connected to the illumination light control circuit 150. The illumination light control circuit 150 transmits a control signal indicating the quantity of light or emitting timing of the laser light to each of the driving circuits DRa to DRe to control each of the light sources LDa to LDe. As a result, each of the light sources LDa to LDe can emit the laser light with an independent quantity of laser light at independent emitting timing. That is, each of the light sources LDa to LDe can be independently caused to oscillate or go off based on an observation mode or a display mode described later.

The laser light emitted from the light sources LDa to LDe enters the light multiplex optical system 141. Details of the light multiplex optical system 141 are omitted in FIG. 1, however, common multiplexing optical technology is applicable to the light multiplex optical system 141. For example, the light multiplex optical system 141 is a space optical system in which a plurality of dichroic mirrors are combined, or an optical combiner in which end faces of a plurality of optical fibers are connected to an end face of a single optical fiber so as to face each other. The following describes an example where the light multiplex optical system 141 is the space optical system.

The laser light emitted from the light sources LDa to LDe is emitted toward the connector 240 via a lens system or the dichroic mirrors not illustrated. That is, the laser light emitted from the light sources LDa to LDe is multiplexed by the light multiplex optical system 141, and resultant multiplexed laser light is emitted from a single emission end toward an incident end of the light guide path 214 disposed in the connector 240. The laser light that has entered the incident end of an optical waveguide is guided by the light guide path 214 to the illumination lenses 211 and 212 at the distal end of the insertion section 210, and is spread by the illumination lenses 211 and 212 at the desired radiation angle to be emitted toward the object.

In order to stabilize the quantities of laser light emitted from the light sources LDa to LDe, the control device 100 includes a laser light quantity monitor not illustrated. The driving circuits DRa to DRe regulate an amount of electric current supplied to semiconductor lasers according to output values of the laser light quantity monitor to cause the light sources to output desired quantities of laser light. A method for regulating the quantities of laser light is not limited to a method using a light quantity monitor. For example, a memory, not illustrated, may store a table indicating a relationship between an electric current and a quantity of light in advance, and the driving circuits DRa to DRe may regulate the electric current to be supplied referring to this table. There are various other known methods for regulating the quantity of light and one of these methods may be selected according to a use.

Furthermore, a laser light source includes a temperature stabilization section for controlling temperature of the semiconductor laser element. The driving circuits DRa to DRe each output a control signal for controlling the temperature stabilization section. A change in temperature of the semiconductor laser element generally changes the quantity of light and wavelength of the laser light oscillated. Thus, in order to obtain the laser light with a stable quantity of light and wavelength, the laser light source includes the temperature stabilization section. For example, the temperature stabilization section is a Peltier element thermally connected to the semiconductor laser element. The driving circuits DRa to DRe each control the Peltier element and provide a control signal and electricity to regulate the temperature of the semiconductor laser to appropriate temperature. The appropriate temperature is 25 degrees centigrade, for example. A method for stabilizing the temperature of the semiconductor laser is not limited to a method using the Peltier element. For example, there are various known methods such as a method using a heat sink having a sufficient heat capacity, or a method using a forced-air cooling means. One of these methods may be selected according to a use. In addition, it is also possible to use a method including measuring the temperature of the semiconductor laser by a temperature sensor, estimating an amount of electric current to be supplied, a quantity of light to be emitted, and a wavelength based on the measured temperature, and regulating the amount of electric current to be supplied to the semiconductor laser element so as to achieve desired values of estimation. A temperature stabilization mechanism may be independently mounted on each of the light sources LDa to LDe, or the plurality of light sources LDa to LDe may be mounted on a single temperature stabilization mechanism.

The illumination light control circuit 150 is electrically connected to the driving circuits DRa to DRe. The illumination light control circuit 150 controls the quantities of light of the light sources LDa to LDe independently or in linkage via the driving circuits DRa to DRe. The emitting timing of each laser light according to the present embodiment will be described later.

The first processing circuit 110 performs image processing of converting an image signal transmitted from the imaging unit 213 via the image signal line 215 into a signal that can be displayed by the display section 300.

The connector 240 makes the image signal line 215, the light guide path 214, and an electric power line, not illustrated, for supplying electricity to the imaging unit 213, electrically or optically attachable to/detachable from the control device 100. In addition, the connector 240 makes electric wiring or optical wiring, which is necessary for the endoscope apparatus to function, electrically or optically attachable to/detachable from the control device 100. Furthermore, the connector 240 makes tube piping or the like attachable to/detachable from the control device 100. The tube piping is used for sending gas or liquid required for observation or operation of treatment using the endoscope apparatus.

The present embodiment indicates an example where each of the light sources LDa to LDe has one semiconductor laser, however, a configuration is not limited to this. A combination of a plurality of laser elements having approximately identical wavelengths may be treated as one laser light source. In this case, a light multiplex section, not illustrated, is disposed in the laser light source to multiplex the laser light emitted from a plurality of laser light sources so as to output the laser light from a single emission end. Alternatively, a number of input ends of the light multiplex optical system 141 in FIG. 1 may be increased according to a number of laser elements.

Mounting a plurality of laser elements on a single laser light source enables acquisition of sufficient quantity of light even when it is impossible to prepare a laser element having a desired wavelength that can provide a sufficient quantity of light, for example. In addition, combining a plurality of low-cost and low-output lasers can implement cost reduction. On the other hand, using one laser element to one laser light source can reduce a size of the main body section. This configuration can also simplify a control system and reduce power consumption.

Next, observation modes are described. Here, in order to acquire an image for display in each observation mode, laser light sources to be caused to emit light differ in each observation mode. However, as will be described later, according to the present embodiment, an image for display and an image for support information extraction are acquired regardless of the observation mode. Thus, the laser light sources to be caused to emit light are practically the same regardless of the observation mode. Furthermore, the image for display differs according to the observation mode, however, the image for support information extraction is the same regardless of a difference in the observation mode.

The endoscope apparatus 10 has a normal light observation mode with white light illumination and a narrow band imaging (NBI) observation mode with NBI illumination. The NBI observation mode is also referred to as a special light observation mode in a broad sense. The normal light observation mode is also referred to as a white light observation mode.

In the normal light observation mode, an observation image is acquired with white light generally used in the endoscope apparatus, and the observation image is displayed on the display section 300. In the NBI observation mode, narrowband light corresponding to absorption characteristics of hemoglobin is used as illumination light to display a blood vessel especially in a surface layer and an intermediate layer of mucosa with high contrast. For example, the operator sets the observation mode using the operation section 220 or the input section 600. The input section 600 is an input device accepting operation input from the operator to the endoscope apparatus 10, and is connected to the control device 100.

Figure 3:
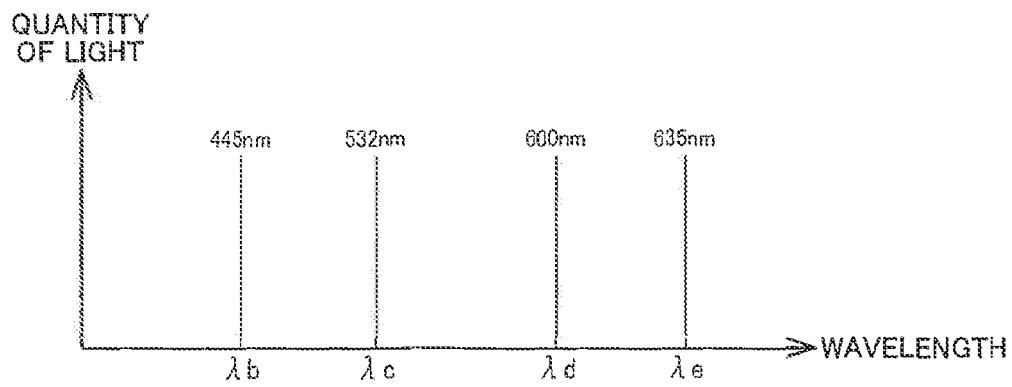
FIG. 3 is an example of laser light for generating a white light image.

As illustrated in FIG. 3, the light source section 140 emits illumination light including four line spectra in the normal light observation mode. That is, the light source section 140 causes four laser light sources of the light sources LDb to LDe to emit light. At this time, a light quantity ratio of the four types of laser light is regulated such that the illumination light becomes white. For example, the light quantity ratio is determined such that color temperature becomes 6000 Kelvin.

Figure 4:
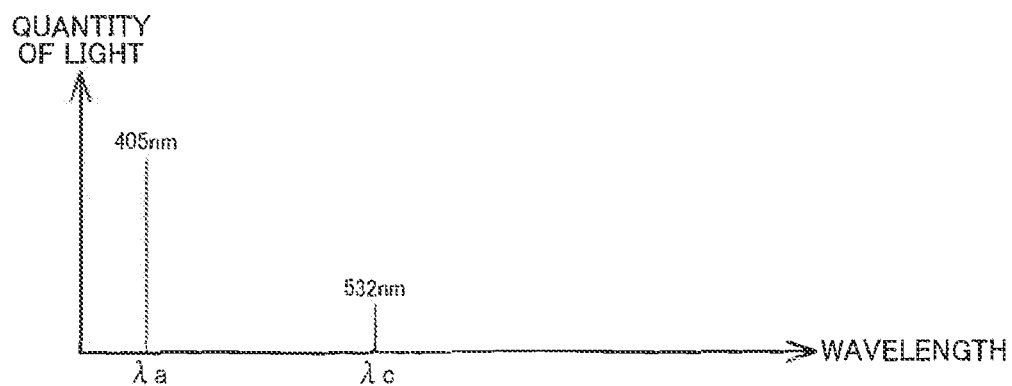
FIG. 4 is an example of laser light for generating an NBI image.

As illustrated in FIG. 4, the light source section 140 emits illumination light including two spectra of 405 nm and 532 nm in the NBI observation mode. These spectra are selected based on absorption spectra of hemoglobin in blood. That is, the light source section 140 causes two laser light sources of the light sources LDa and LDc to emit light. At this time, a light quantity ratio of these two types of laser light is set to a light quantity ratio appropriate to the NBI observation mode. The light quantity ratio is set in advance. For example, a ratio of a quantity of light emission of the light source LDa to a quantity of light emission of the light source LDc is set three to one.

2. First Embodiment

The endoscope apparatus 10 can simultaneously acquire images in two observation modes including the normal light observation mode and the NBI observation mode. A procedure for this is described.

The endoscope apparatus 10 approximately simultaneously acquires the images in the normal light observation mode and the NBI observation mode.

Specifically, in order to generate an image in the normal light observation mode, four images with illumination light of four colors including B, G, A, and R need to be acquired. In order to generate an image in the NBI observation mode, two images with illumination light of two colors including V and G need to be acquired. Five colors of V, B, G, A, and R respectively correspond to wavelengths of 405, 445, 532, 600, and 635 nm in FIG. 2.

Two colors of A and R are generally included in a red region. That is, the two colors are included in a wavelength band transmitted by a red color filter of the image sensor. Accordingly, if the illumination light in these two colors are simultaneously emitted, a single R image is acquired. In the endoscope apparatus 10 according to the present embodiment, laser light in A color and laser light in R color are emitted at different timings so as to separately acquire an A image and an R image. Furthermore, as illustrated in FIGS. 3 and 4, a quantity of light in G color in the white light image differs from a quantity of light in G color in the NBI image. In the endoscope apparatus 10 according to the present embodiment, these images are also separately acquired. In the following description, the quantity of light in G color for generating the white light image is referred to as a light quantity 1 and the quantity of light in G color for generating the NBI image is referred to as a light quantity 2. The endoscope apparatus 10 according to the present embodiment approximately simultaneously acquires six images of a B image, a G image with the light quantity 1, the A image, the R image, a V image, a G image with the light quantity 2. Then, the endoscope apparatus 10 generates the white light image and the NBI image based on an image processing sequence, described later, and displays the images. Accordingly, the illumination light control circuit 150 causes the light sources LDa to LDe to emit light based on a light emission sequence as illustrated in FIG. 3. This sequence is described in detail referring to FIG. 5.

Figure 5:
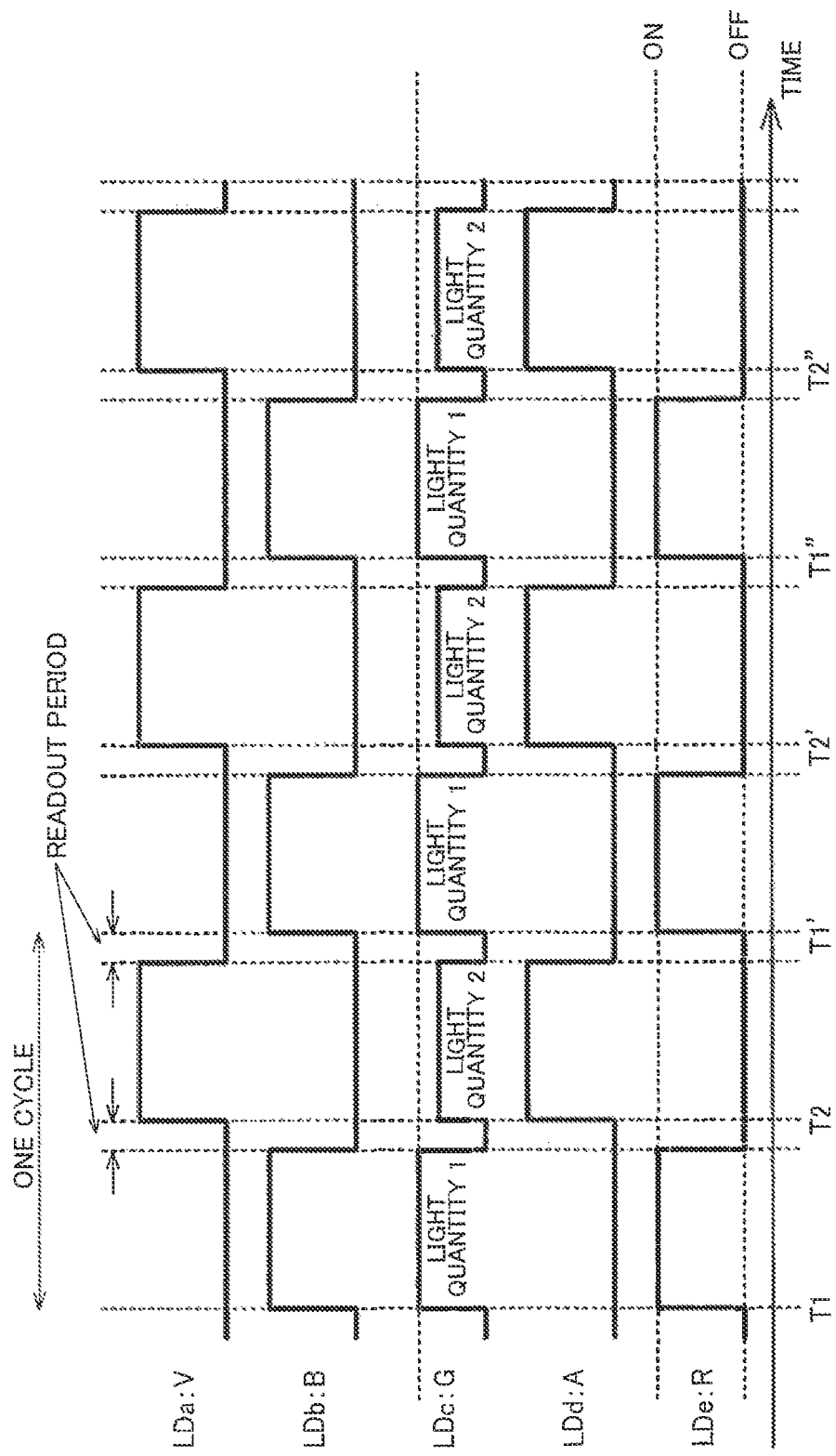
FIG. 5 is a light emission sequence of illumination light in a first embodiment.

In FIG. 5, a horizontal axis represents time. Timings of light emission and extinction are shown in an order of the light sources LDa, LDb, LDc, LDd, and LDe from top to bottom in a vertical direction. T1, T2, and so on represent timings. The word "timing" is hereinafter abbreviated to T1, T2 and so on.

The endoscope apparatus acquires both the white light image and the NBI image in one cycle from T1 to T1'. At this time, the image sensor performs image capturing operation twice. That is, one cycle includes two imaging frames.

The illumination light control circuit 150 causes the light sources LDb, LDc, and LDe to emit light in a period from T1 to T2 excluding a readout period by the image sensor. At this time, the illumination light control circuit 150 causes the light source LDc to emit light in G color with the light quantity 1 in the normal light observation mode. The image sensor is an RGB image sensor including primary color filters. Accordingly, blue light from the light source LDb is detected by a B pixel, and thus is output as the B image. Similarly, the G image is output based on green light from the light source LDc, and the R image is output based on red light from the light source LDe. The G image used here is the G image with the light quantity 1. This image information is output from the image sensor during the readout period when all the light sources LDa to LDe are extinguished.

Then, the illumination light control circuit 150 causes the light sources LDa, LDc, and LDd to emit light in a period from T2 to T1'. At this time, the illumination light control circuit 150 causes the light source LDc to emit light in G color with the light quantity 2 in the NBI observation mode. The V image is output based on violet light from the light source LDa, the G image is output based on green light from the light source LDc with the light quantity 2, and the A image is output based on orange light from the light source LDd. This image information is output from the image sensor during the readout period.

The illumination light control circuit 150 continuously repeats operation in one cycle described above. As a result, four images required to generate the white light image and two images required to generate the NBI image are acquired in one cycle.

Next, operation performed by the first processing circuit 110 is described.

The first processing circuit 110 generates the white light image and the NBI image from the six images acquired based on the sequence described above. The first processing circuit 110 also outputs one or more of the six images to a diagnosis support section 121 of the second processing circuit 120.

Specifically, the first processing circuit 110 generates an RGB image signal for display from the B image, G image with the light quantity 1, A image, and R image, and outputs the RGB image signal to the display section 300.

The first processing circuit 110 also generates an RGB image signal for display from the V image and the G image with the light quantity 2, and outputs the RGB image signal to the display section 300. As a result, the NBI image that is a color image in the NBI observation mode can be displayed on a monitor.

Next, the display section 300 is described.

The display section 300 displays an object image applied with the image processing by the first processing circuit 110. The display section 300 is one of various common display devices, and is a liquid crystal monitor, for example.

The display section 300 and the control device 100 are electrically connected by an electrical line. The image signal output from the first processing circuit 110 is transmitted to the display section 300 through the electrical line. The display section 300 displays the received image information.

In FIG. 1, the electrical line connecting the display section 300 and the control device 100 is illustrated by a single line, however, a configuration is not limited to this. Two or more electrical lines may be used as needed. Furthermore, essential members, such as a power line for supplying electricity required for operation of the display section 300, are omitted in FIG. 1. A method for transmitting the image signal is not limited to the electrical line, and various kinds of common signal transmission technology, such as radio communication or optical communication, may be used.

The endoscope apparatus 10 according to the present embodiment can display the white light image and the NBI image as described above. The endoscope apparatus 10 according to the present embodiment can simultaneously display these two images in parallel, or can also display one of the images according to the observation mode selected by the operator. In addition, the endoscope apparatus 10 can implement various display modes implemented by conventional endoscope apparatuses having a plurality of observation modes.

Next, the second processing circuit 120 is described.

The second processing circuit 120 includes the diagnosis support section 121. The diagnosis support section 121 is the AI, for example. That is, the diagnosis support section 121 extracts the diagnosis support information from the input one or more images by AI processing. The AI processing can include various image recognition methods or machine learning methods. The machine learning method is a process of making various inferences based on learning results. A representative example of the AI is a neural network. However, the AI is not limited to this, and various known machine learning methods may be used as the AI in the present embodiment.

The diagnosis support section 121 generates the diagnosis support information based on the image signal acquired by the imaging unit 213. Specifically, the diagnosis support section 121 generates the diagnosis support information based on the one or more of the six images selected by the first processing circuit 110 described above. The diagnosis support information is information that supports the operator in making a diagnosis. That is, the diagnosis support information is information about a target portion that is present in the image and is a target of the observation. For example, the target portion is cancer or a lesion part in an examination using the endoscope apparatus. The diagnosis support information includes information such as a position, size, shape, or contour of the target portion. Alternatively, when the target portion is the cancer, the diagnosis support information includes information such as a progression degree or stage level of the cancer. The diagnosis support information may be a combination of a plurality of types of the information described above.

Providing the diagnosis support information to a physician can support the physician in making a diagnosis. The diagnosis support section 121 extracts the diagnosis support information based on one or more of the six images acquired approximately simultaneously by the imaging unit 213. A procedure for extracting the support information will be described later.

The diagnosis support section 121 transmits the extracted diagnosis support information to the first processing circuit 110. The first processing circuit 110 adds display information corresponding to the diagnosis support information to the display image, and transmits a resultant display image to the display section 300. The display information added to the display image is hereinafter referred to as support display information. The support display information is displayed with the white light image in the normal light observation mode, and with the NBI image in the NBI observation mode. At this time, the diagnosis support information is generated based on the same image or images in both the observation modes. Accordingly, the operator can confirm and appreciate the diagnosis support information without a sense of incongruity.

Next, basic operation of the endoscope apparatus 10 is described.

The endoscope apparatus 10 is firstly supplied with power by the operator. After the power is supplied, the endoscope apparatus 10 checks whether the apparatus is in a normal state using a self-check circuit or the like, similarly to common endoscopes. After confirmation of the normal state, predetermined electric currents are applied from the driving circuits DRa to DRe to the light sources LDa to LDe to perform warm-up operation to stabilize the laser light sources.

The scope section 200 stored as a separate body separated from the control device 100 is taken out by the operator, and the connector 240 of the scope section 200 is connected to the control device 100. The control device 100 checks a connection state of the scope, a type of the connected scope section 200, or the like, similarly to common endoscopes.

After confirmation of the connection of the scope section 200, the illumination light control circuit 150 transmits the control signals to the driving circuits DRa to DRe based on the light emission sequence illustrated in FIG. 5 so as to cause the light sources LDa to LDe to emit light. The control device 100 includes the memory, not illustrated, and the memory stores information about basic characteristics or individual differences of the light sources LDa to LDe. The driving circuits DRa to DRe refer to the information to control the light sources LDa to LDe. The information includes, for example, information about a relationship between a driving current and a quantity of light emission of each laser light source, and information about a relationship between a driving current and an oscillation wavelength. The illumination light control circuit 150 sequentially transmits the control signals to the light sources LDa to LDe. The driving circuits DRa to DRe refer to a timing circuit, not illustrated, or the like included in the control device 100 to synchronize the light sources LDa to LDe one another so as to cause the light sources LDa to LDe to emit light with the quantities of light and at timings indicated in FIG. 5.

The light sources LDa to LDe perform laser oscillation according to the driving currents applied by the driving circuits DRa to DRe, and emit the laser light each having a predetermined wavelength. The laser light emitted from the light sources LDa to LDe is multiplexed by the light multiplex optical system 141, and the multiplexed laser light enters the incident end of the optical fiber bundle. The laser light that enters the optical fiber bundle is guided to the illumination lenses 211 and 212, and is emitted from the illumination lenses 211 and 212 toward the object. The imaging unit 213 captures an image of the object irradiated by this illumination light.

The first processing circuit 110 receives the image signal transmitted from the imaging unit 213 via the image signal line 215, and performs appropriate image processing to the image signal. The image processing differs according to the observation mode. A relationship between the observation mode and the image processing to be applied is stored in a memory, not illustrated, disposed in the first processing circuit 110, for example. Alternatively, the relationship is stored in the memory, not illustrated, in the control device 100. The first processing circuit 110 performs the image processing to the image signal to generate the V image, B image, G image with the light quantity 1, G image with the light quantity 2, A image, and R image.

The diagnosis support section 121 generates the diagnosis support information by the AI processing based on the V image and G image which can show the blood vessel with high contrast. The G image used here is the G image with the light quantity 1. The display image in the NBI observation mode is generated by combining the V image and the G image with the light quantity 2. Thus, a combination of the images that is different from a combination used to generate the NBI image is input to the diagnosis support section 121. According to the present embodiment, the images with the wavelengths allowing detection of hemoglobin, i.e., the blood vessel, with high contrast are selected. Thus, the diagnosis support information is generated based on a pattern or distribution of the blood vessel. For example, a presumable target portion includes the cancer.

The V image and the G image are input for the AI processing as individual images, not as a combined image. That is, the diagnosis support section 121 extracts the target portion from each of the V image and the G image. When the target portion is present, the diagnosis support section 121 generates the diagnosis support information of the target portion. When the target portion is extracted, the diagnosis support section 121 stores a position, a contour, or the like of the target portion in a memory, not illustrated. The diagnosis support section 121 stores this information for each of the V image and the G image in the memory. The diagnosis support section 121 estimates whether the extracted target portion is the cancer. When the target portion is the cancer, the diagnosis support section 121 estimates the progression degree or stage level of the cancer. The diagnosis support section 121 outputs these estimation results as the diagnosis support information. As for a method for generating the diagnosis support information, common or available AI technology may be used. As for preparation or selection of training data when the machine learning is used, various types of known technology may be used.

The diagnosis support information may include information listed below, for example. One or a combination of a plurality of types of information described below is used as the diagnosis support information.

(1) information about a position: a position, shape, contour of the target portion The contour is, for example, a demarcation line dividing the cancer from normal cells (2) information about a configuration: whether the target portion is convex, flat, or concave Alternatively, whether the target portion is pedunculated, or the like (3) information about a state: whether the target portion is scattered or stays in one place When the target portion is scattered, density of the target portion, a size of each target portion, or the like (4) other information: bleeding or not, a mark or a scar of treatment or surgery, whether *Helicobacter pylori* has been removed, or the like The diagnosis support information may be the information (1) to (4) itself, or information determined by comprehensively evaluating the information (1) to (4). For example, the diagnosis support information may include information (5) and (6) below.

(5) information about medical characteristics: whether the target portion is the cancer When the target portion is the cancer, whether the cancer is benign or malignant, or which stage of I to IV the cancer is in (6) information about treatment: a treatment method, a surgery method, medication appropriate for the target portion, or the like Alternatively, information about a recommended additional examination, a pathological state, or the like For example, data including the information (1) to (6) described above and image information associated to the information (1) to (6) are used as the training data, so that the information (1) to (6) can be obtained as output of the AI processing.

Alternatively, the diagnosis support section 121 may perform the AI processing as a first process and then further perform a subsequent second process. In this case, the AI processing uses data including the information (1) to (4) and the image information associated to the information (1) to (4) as the training data. The AI processing outputs the information (1) to (4) as output. The second process generates the information (5) and (6) described above based on the information (1) to (4) output by the AI processing. For example, the second process is generated by following a method used by the physician based on the information (1) to (4). The second process is implemented by the AI or information processing without the AI, for example.

Since the diagnosis support information is extracted from each of the V image and the G image, the diagnosis support information extracted from the V image and the diagnosis support information extracted from the G image may differ. For example, the target portion may be extracted only from one of these images. Alternatively, even when target regions are extracted from both images, the contours or positions of the target regions may differ between the images. In this case, the diagnosis support information of the respective target regions may be separately presented to the operator to let the operator determine. Alternatively, the information may be used as new input for the AI processing, and the AI processing may generate comprehensive diagnosis support information as final output.

Next, a method for presenting the diagnosis support information to the operator is described.

The endoscope apparatus 10 displays the support display information on a display image desired by the operator, or an image set by default. That is, it is not necessary to display the diagnosis support information with original images used to extract the diagnosis support information. The endoscope apparatus 10 displays the support display information with the white light image in the white light observation mode, and with the NBI image in the NBI observation mode.

For example, the first processing circuit 110 superimposes the support display information indicating the position or contour on the display image based on the diagnosis support information about the position or contour. According to the present embodiment, the six images are acquired approximately simultaneously as described above, and thus each of the images is an image captured at approximately the same position and angle. Thus, the information about the position and contour of the target portion extracted from one of the images is approximately the same as the information about the positions and contours extracted from remaining images. Accordingly, it is possible to omit a procedure for calculating a positional relationship of respective images to align the positions of the target portions. Needless to say, it is possible to calculate position information among the images by known technology to align the images such that the positions and contours indicate identical portions.

The information other than the position and contour may be displayed in a region of a region where the object image is displayed on a screen of the display section 300. Alternatively, the information may be superimposed on the object image. Alternatively, other various known display methods may be used.

According to the present embodiment, one or some of the captured images are input for the AI processing. Accordingly, compared with a case where all the six images are used, the diagnosis support information can be generated in a short time.

In addition, the images used to extract the target portions and the images used to generate the display image differ at least by one image. According to the present embodiment, the diagnosis support information is extracted from the V image and the G image with the light quantity 1. The display image in the normal light observation mode is generated from the B image, G image with the light quantity 1, A image, and R image. That is, the display image does not include the V image. The display image in the NBI observation mode is generated from the V image and the G image with the light quantity 2. That is, the display image does not include the G image with the light quantity 1. In other words, the images suitable for extraction of the diagnosis support information by the AI processing are input for the AI processing. On the other hand, the images suitable for observation by people are used for generating the display image.

The display section 300 can display various information such as information about the observation mode input from the input section 600, information about an observation target, an observation date, or time taken for observation. This information is supplied from a memory, a clock, or a timer, not illustrated, disposed in the scope section 200 or the control device 100. Alternatively, this information is input from the input section 600.

For example, the images suitable for extraction of the support information by the AI do not necessarily correspond to the images suitable for diagnosis or examination by people. Accordingly, it is necessary to prioritize one of operations of displaying the images easy to watch by people and inputting the images suitable for extraction of the support information by the AI. For example, since it is people that make a diagnosis, displaying the images easy to watch by people is generally prioritized. In this case, the AI extracts the support information from the images easy to watch by people.

Alternatively, when the support information is extracted from a special light image as disclosed in JP-A-2016-144626 and JP-A-2012-152279, the observation mode needs to be switched to a special light mode to obtain the support information. Even if the support information is extracted from a white light image in a white light mode, an image or images input to the AI differ according to the mode. Thus, the support information provided in the normal observation mode and the special light mode may differ. Meanwhile, the support information is required at various scenes. For example, it is necessary to display the support information on the white light image for screening, and on the special light image for magnifying observation of the lesion part.

According to the embodiment described above, the endoscope apparatus 10 includes the imaging section, the light source section 140, and the first processing circuit 110. The imaging section captures an image of the object. The light source section 140 emits first to m-th light (m is an integer of two or more) with different colors as the illumination light for the object. The first processing circuit 110 generates first to n-th images (n is an integer of two or more) based on the image signal from the imaging section. Each of the first to n-th images corresponds to any one of the first to m-th light. The first processing circuit 110 generates the display image based on a display image group including some images of the first to n-th images. The first processing circuit 110 also outputs a support image different from the display image, or a support image group that is at least partly different from the display image, to the second processing circuit 120. Then, the first processing circuit 110 acquires the diagnosis support information. The diagnosis support information is output from the second processing circuit 120 based on the support image or the support image group.

In FIG. 1, the imaging section corresponds to the imaging unit 213. In a first embodiment, m is five (m=5), however, an applicable target of the present disclosure is not limited to m=5. In the first embodiment, n is six (n=6), and the first to n-th images are the V image, B image, G image with the light quantity 1, G image with the light quantity 2, A image, and R image. However, an applicable target of the present disclosure is not limited to n=6. In addition, a relation is not limited to n≠m, and the relation may be n=m. For example, when respective light sources are caused to emit light once in one cycle, the relation of n=m is realized. When one light source is caused to emit light twice with different light quantities as in the first embodiment, the relation of n≠m is realized. Furthermore, in the first embodiment, the display image group includes the B image, G image with the light quantity 1, and R image, and the support image group includes the V image and the G image with the light quantity 1. The support image group does not include the display image. In a second embodiment described later, the support image is an IR image which is different from the display image. The support image group only needs to at least partly differ from the display image. That is, the support image group is an image group that does not include the display image, or that includes the display image and one or more of the first to n-th images. FIG. 1 describes an example where the second processing circuit 120 is included in the endoscope apparatus 10, however, the second processing circuit 120 may be disposed outside the endoscope apparatus 10, as will be described later referring to FIG. 10. That is, the present disclosure is applicable to a case where the second processing circuit 120 is not embedded in the endoscope apparatus 10.

According to the present embodiment, the support image different from the display image, or the support image group that is at least partly different from the display image is input to the second processing circuit 120, and the second processing circuit extracts the diagnosis support information from the support image or the support image group. As a result, it is possible to respectively provide a most suitable image or images for the image information used to generate the diagnosis support information by the AI technology and for the image information used to generate the observation image for observation operation. As for generation of the diagnosis support information, a minimum and most suitable image or images can be selected. As a result, faster, more efficient, and highly accurate generation of the diagnosis support information can be expected. As for generation and display of the observation image for the operator, most suitable image information is selected for each observation mode. Therefore, it is possible to generate an image with quality as desired by the operator in color reproductivity, image quality, resolution, contrast of the lesion part, or the like.

According to the first embodiment, the display image group differs from the support image group, however, a configuration is not limited to this, and the display image group may be the same as the support image group. The display image is generated by combining the images in the display image group, and thus the display image differs from each of the images in the display image group. Accordingly, even when the support image group is the same as the display image group, the support image group does not include the display image itself. For example, in a third embodiment described later, the display image group includes the G image with the light quantity 1, A image, and R image, and an RBI image is generated as the display image by combining these images. In this case, the support image group includes the G image, A image, and R image, and these three images are separately input for the AI processing. That is, the RBI image generated by combining the three images differs from the three separate images in the support image group.

Furthermore, according to the present embodiment, the first processing circuit 110 generates a first display image based on a first display image group when a first display mode is set. The first processing circuit 110 generates a second display image based on a second display image group when a second display mode is set. The first display image group and the second display image group include images selected from the first to n-th images. The second display image group differs from the first display image group. The first processing circuit 110 outputs the support image different from the first display image and the second display image, or the support image group that is at least partly different from the first display image and the second display image, to the second processing circuit 120.

In the first embodiment, the first display mode is the normal light observation mode, and the second display mode is the NBI observation mode. That is, the first display image is the white light image, and the second display image is the NBI image. The first display image group includes the B image, G image with light quantity 1, A image, and R image, and the second display image group includes the V image and the G image with the light quantity 2. The support image group includes the V image and the G image with the light quantity 1 that differ from the white light image and the NBI image. The support image group only needs to at least partly differ from the first display image and the second display image.

According to the present embodiment, when the display mode can be selectively set from a plurality of display modes, the support image or the support image group different from the display images in the plurality of display modes is input to the second processing circuit 120. At this time, the support image or the support image group is the same in the plurality of display modes. As a result, the diagnosis support information is extracted from the same image or image group regardless of the display mode, and the support display information based on the diagnosis support information can be displayed on the display section 300. That is, the diagnosis support information can be extracted from the image or image group that is most suitable for extraction of the support display information regardless of the display mode. In addition, the diagnosis support can be always performed based on the same image or image group regardless of the display mode set by the operator. The first processing circuit 110 may output the support image different from the first display image, or the support image group that is at least partly different from the first display image, to the second processing circuit 120 when the first display mode is set. That is, the support image may be the second display image or the support image group may include the second display image in the first display mode. The first processing circuit 110 may also output the support image different from the second display image, or the support image group that is at least partly different from the second display image, to the second processing circuit 120 when the second display mode is set. That is, the support image may be the first display image or the support image group may include the first display image in the second display mode. Even in this case, effects similar to those described above can be obtained.

Furthermore, according to the present embodiment, the support image is one of the first to n-th images, an image generated by combining some of the first to n-th images, or an image generated by combining all the first to n-th images. The support image group includes some images selected from the first to n-th images.

In the second embodiment described later, the support image is the IR image. In this case, the support image is one of the first to n-th images. Furthermore, as a modification example of the first embodiment, the support image may be a combined image generated by combining the V image and the G image with the light quantity 1. In this case, the support image is the image generated by combining some of the first to n-th images. The support image may be the image generated by combining all the first to n-th images. Furthermore, in the first embodiment, the support image group includes the V image and the G image with the light quantity 1. In this case, the support image group includes the images selected from the first to n-th images. Furthermore, in the third embodiment described later, the display image group includes the G image with the light quantity 1, A image, and R image, and the support image group is identical. Also in this case, the support image group includes the images selected from the first to n-th images.

According to the present embodiment, the image or the image group that is most suitable for generation of the diagnosis support information by the AI technology can be input for the AI processing. In addition, the display image can be generated from the images that are most suitable for generation of the observation image.

Furthermore, according to the present embodiment, the imaging section includes the image sensor having color filters of blue, green, and red. m is four or more. First light has a peak wavelength in a transmission wavelength band of the blue color filter, second light has a peak wavelength in a transmission wavelength band of the green color filter, and third light has a peak wavelength in a transmission wavelength band of the red color filter. Fourth light has a peak wavelength in any one of the transmission wavelength bands of the blue color filter, green color filter, and red color filter. The light source section 140 emits some of the first to fourth light that passes through the same color filter in different imaging frames.

In the first embodiment, the first light is blue laser light having a wavelength $\lambda b=445$ nm, the second light is green laser light having a wavelength $\lambda c=532$ nm, and the third light is red laser light having a wavelength $\lambda e=635$ nm. The fourth light is violet laser light having a wavelength $\lambda a=405$ nm, for example. Alternatively, the fourth light may be orange laser light having a wavelength $\lambda d=600$ nm. Alternatively, the fourth light may be the green laser light having the wavelength $\lambda c=532$ nm, and the quantity of light may differ from the quantity of light of the second light. In the first embodiment, the light source section 140 emits the first to third light in an imaging frame between T1 and T2, and the fourth light in an imaging frame between T2 and T1'.

According to the present embodiment, the light source section 140 simultaneously emits the light that can be divided by the RGB filters of the image sensor, and emits the light that passes through the same color filter in different imaging frames. As a result, it is possible to capture the first to n-th images as quickly as possible using the color image sensor having the RGB filters arranged in Bayer alley, for example. That is, when the first to fourth light is sequentially emitted, four imaging frames are required. However, only two imaging frames are required in the present embodiment. With this configuration, all the images used for the AI technology and display can be acquired approximately simultaneously. As a result, the position and contour of the target portion extracted as the diagnosis support information approximately correspond to the position and contour in the display image. Accordingly, it is possible to display the diagnosis support information and the observation image in layers, for example, by superimposing the diagnosis support information on the observation image without any complicated alignment technology.

Furthermore, according to the present embodiment, the light source section 140 emits the first light, second light, and third light in a first imaging frame. The light source section 140 also emits the fourth light in a second imaging frame. The second imaging frame is an imaging frame after or before the first imaging frame. That is, the second imaging frame is an imaging frame adjacent to the first imaging frame immediately before or after.

In FIG. 5, assuming that the imaging frame between T1 and T2 is the first imaging frame, the imaging frame between T2 and T1' is the second imaging frame after the first imaging frame. In the first embodiment, one cycle includes two imaging frames, however, one cycle may include three or more imaging frames. In this case, the second imaging frame may be before or after the first imaging frame. For example, in a light emission sequence described later referring to FIG. 8, assuming that an imaging frame between T3 and T1' is the second imaging frame, the second imaging frame is present before the first imaging frame between T1' and T2'.

According to the present embodiment, the first to n-th images are acquired in the first imaging frame and the second imaging frame adjacent to the first imaging frame immediately before or after. As a result, the first to n-th images can be acquired approximately simultaneously.

Furthermore, according to the present embodiment, the fourth light is narrowband light having a wavelength band narrower than the transmission wavelength band of the blue color filter, green color filter, or red color filter. Furthermore, according to the present embodiment, n is four or more. The display image group includes first to third images respectively corresponding to the first to third light. When the first processing circuit 110 outputs the support image, the support image is a fourth image corresponding to the fourth light. When the first processing circuit 110 outputs the support image group, the support image includes the fourth image corresponding to the fourth light.

According to the present embodiment, the fourth image captured with the narrowband light can be input to the second processing circuit 120. The narrowband light only includes information of the object in a narrow wavelength band. For example, a wavelength of light determines a depth from a tissue surface that the light can reach. That is, using the narrowband light allows acquisition of the object image at a specific depth. The wavelength of the narrowband light is selected according to contents of the diagnosis support information to be acquired, so that the image or images suitable for extraction of the diagnosis support information can be input for the AI processing.

Furthermore, according to the present embodiment, the light source section 140 includes first to fourth light sources. A first light source emits the first light which has the peak wavelength in a range from 436 to 480 nm. A second light source emits the second light which has the peak wavelength in a range from 481 to 585 nm. A third light source emits the third light which has the peak wavelength in a range from 616 to 700 nm. A fourth light source emits the fourth light which has the peak wavelength in a range from 400 to 435 nm. The light source section 140 causes the first to third light sources to emit light in the first imaging frame, and the fourth light source in the second imaging frame.

In FIGS. 1 and 5, the first light source corresponds to the light source LDb, the second light source to the light source LDc, the third light source to the light source LDe, and the fourth light source to the light source LDa.

According to the present embodiment, the light source section 140 includes the first to fourth light sources, so that the light source section 140 can emit the first light having the peak wavelength in the wavelength band of the blue color filter, the second light having the peak wavelength in the wavelength band of the green color filter, the third light having the peak wavelength in the wavelength band of the red color filter, and the fourth light having the peak wavelength in the wavelength band of the blue color filter. Furthermore, each of the light is emitted from each of the independent light sources, so that the light emission sequence can be implemented by on-off control of the light sources. For example, when a laser light source or an LED is used, a quantity of light emission of a light source can be made zero by turning off the light source. That is, the illumination light can be light with high purity including only light emitted from a light source turned on.

Furthermore, with the fourth light source that emits the violet laser light, the NBI observation mode can be implemented together with the green laser light. In the NBI observation mode, the blood vessel in the surface layer of the mucosa can be observed with high contrast. Furthermore, the support image group includes the images captured with the violet laser light and the green laser light, so that the diagnosis support information can be extracted from the images including the blood vessel in the surface layer of the mucosa with high contrast.

Furthermore, according to the present embodiment, in the second imaging frame, the light source section 140 causes the second light source to emit light with the quantity of light emission different from the quantity of light emission of the second light source in the first imaging frame so as to emit fifth light. The first display image group includes the first to third images corresponding to the first to third light. The second display image group includes the fourth image and a fifth image corresponding to the fifth light. The support image group includes the second image and the fourth image corresponding to the fourth light. When the first display mode is set, the first processing circuit 110 generates the first display image based on the first display image group, and outputs the support image group to the second processing circuit 120. When the second display mode is set, the first processing circuit 110 generates the second display image based on the second display image group, and outputs the support image group to the second processing circuit 120.

In the first embodiment, the light source section 140 causes the light source LDc to emit light with the light quantity 1 in the first imaging frame and with the light quantity 2 in the second imaging frame. The second light is the green laser light with the light quantity 1 and the fifth light is the green laser light with the light quantity 2. The first processing circuit 110 outputs the V image and the G image with the light quantity 1 to the second processing circuit 120 as the support image group. The first display image group includes the B image, G image with the light quantity 1, and R image. The second display image group includes the V image and the G image with the light quantity 2.

According to the present embodiment, the support image group partly differs from both the first display image group and the second display image group. That is, the support image group includes the images that are at least partly different from the images used for generating the display image. This support image group is input for the AI processing, and the diagnosis support information is extracted from the support image group.

Furthermore, according to the present embodiment, the endoscope apparatus 10 includes the second processing circuit 120. The second processing circuit 120 extracts the diagnosis support information from each of the images in the support image group.

For example, the second processing circuit 120 can output the diagnosis support information of each of the images to the first processing circuit 110. Alternatively, the second processing circuit 120 can further extract the diagnosis support information based on the diagnosis support information of each of the images, and output resultant diagnosis support information to the first processing circuit 110. As for the display image, the RGB image needs to be generated to facilitate observation by people, for example. On the other hand, a combined image does not necessarily need to be input for the AI processing. According to the present embodiment, the diagnosis support information can be extracted from the individual images captured in the respective wavelengths.

Furthermore, according to the present embodiment, the endoscope apparatus 10 includes the display section 300 that displays the display image. The diagnosis support information includes information about at least one of the position and contour of the target portion included in the object. The first processing circuit 110 performs the image processing of adding the display information indicating the at least one of the position and contour of the target portion to the display image based on the diagnosis support information, and outputs a resultant display image to the display section 300. The display information corresponds to the support display information described above.

According to the present embodiment, the information about the at least one of the position and contour of the target portion can be extracted as the diagnosis support information. Then, the display information indicating the at least one of the position and contour of the target portion can be presented to the operator. As a result, the diagnosis support can be implemented.

Furthermore, according to the present embodiment, the second processing circuit 120 may output the diagnosis support information including an image. That is, when the second processing circuit 120 extracts the target portion, the second processing circuit 120 outputs position information of the target portion and an image of the target portion as the diagnosis support information. The first processing circuit 110 superimposes the image of the target portion included in the diagnosis support information on a position of the target portion in the display image based on the position information.

Furthermore, according to the present embodiment, the second processing circuit 120 may compare diagnosis support information extracted from each of the images in the support image group, classify the diagnosis support information based on an extraction situation, and output a classification result to the first processing circuit 110 as the diagnosis support information. The extraction situation includes, for example, whether identical target portions are extracted from all the images, whether an identical target portion is extracted from only one image, or which wavelength of the illumination light is used to capture the image including the extracted target portion. The classification is based on, for example, a level of possibility of being cancer, a level of infiltration of the cancer, a stage of the cancer, or the like.

Furthermore, according to the present embodiment, the second processing circuit 120 may classify the target portion based on a currently utilized medical classification, and extract information associating the target portion with a classification result as the diagnosis support information. The medical classification is a common classification such as a TNM classification, a pit pattern classification, or a JNET classification. The TNM classification is widely used to classify a level of progression of the cancer and classifies the cancer into eight levels of IA, IB, IIA, IIB, IIIA, IIIB, IIIC, and IV based on a depth of the cancer, presence of lymph node metastasis and a range thereof, and presence of distance metastasis. The pit pattern classification is based on patterns of surface fine structures of tissue and includes six patterns of type I, II, IIIS, IIIL, IV, and V. The JNET classification is an NBI magnifying endoscopic collective observation classification aiming at qualitative diagnosis such as tissue and an invasion depth of a large intestine tumor, and includes four categories of type 1, 2A, 2B, and 3. These classifications include classifications that can not be determined only by images such as presence of metastasis in another organ. However, for example, the diagnosis support section may be trained with training data associating images with the above described medical classifications in the machine learning so as to be able to perform the classification or provide the diagnosis support information including a possibility of belonging to a level, a pattern, or a category of the classifications. As for the classification, various conventional methods by the AI can be applicable in addition to the machine learning.

3. Second Embodiment

Next, the second embodiment is described. The description that is common to that of the first embodiment is omitted.

Figure 6:
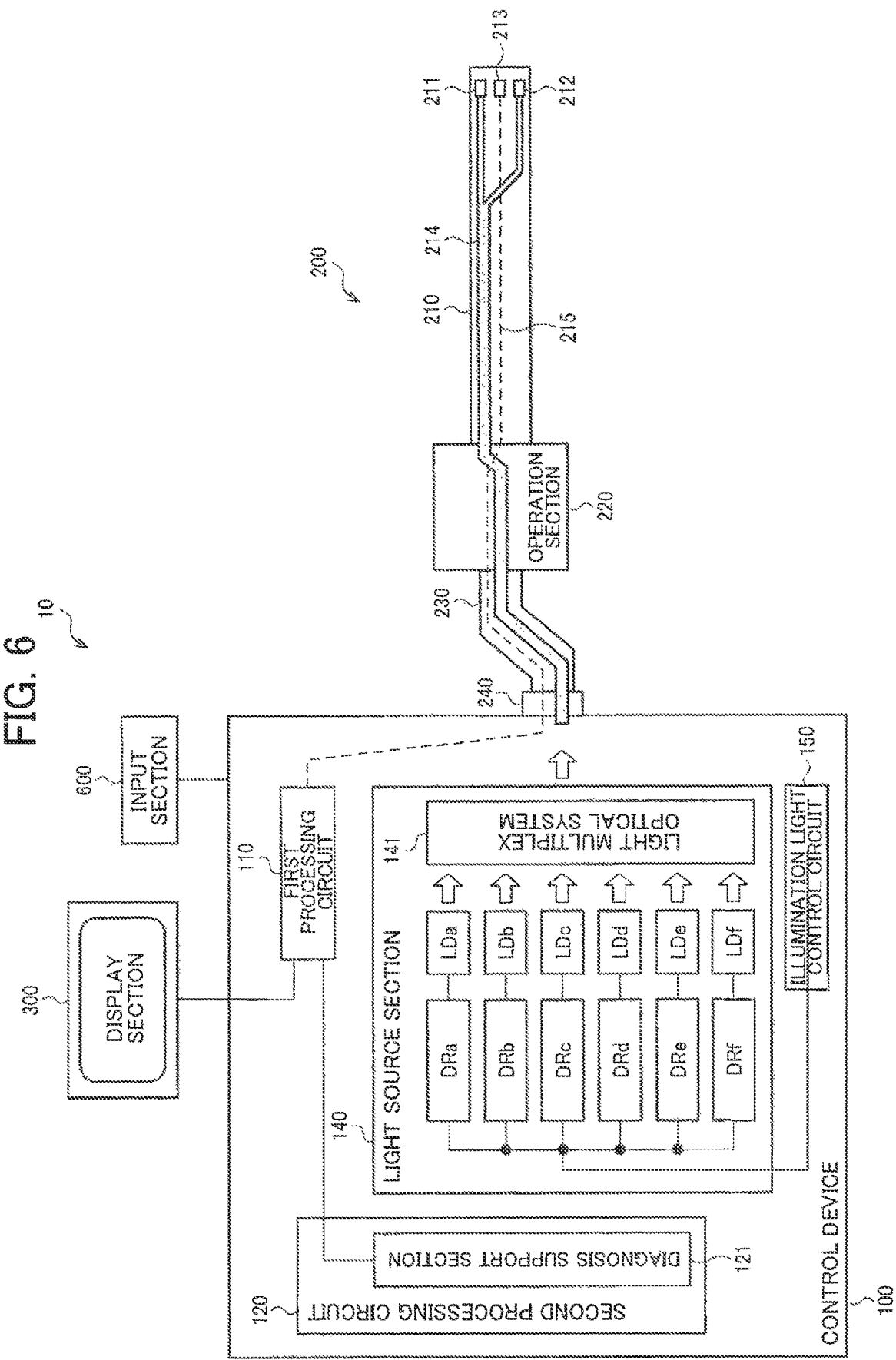
FIG. 6 is a second configuration example of the endoscope apparatus.

FIG. 6 is a second configuration example of the endoscope apparatus 10. In FIG. 6, the light source section 140 includes light sources LDa to LDf, driving circuits DRa to DRf, and the light multiplex optical system 141. The second embodiment differs from the first embodiment in that the light source section 140 includes the light source LDf that emits infrared laser light.

The driving circuit DRf drives the light source LDf. The light multiplex optical system 141 multiplexes the laser light emitted from the light sources LDa to LDf, and causes a resultant multiplexed light to enter the light guide path 214. Details of the driving circuits DRa to DRe are the same as those of the driving circuits DRa to DRe in the first embodiment. The driving circuit DRf also has a function similar to that of the respective driving circuits DRa to DRe in the first embodiment. The light multiplex optical system 141 multiplexes five laser light in the first embodiment, however, the light multiplex optical system 141 multiplexes six laser light in the second embodiment. A multiplexing method is the same as that in the first embodiment.

Figure 7:
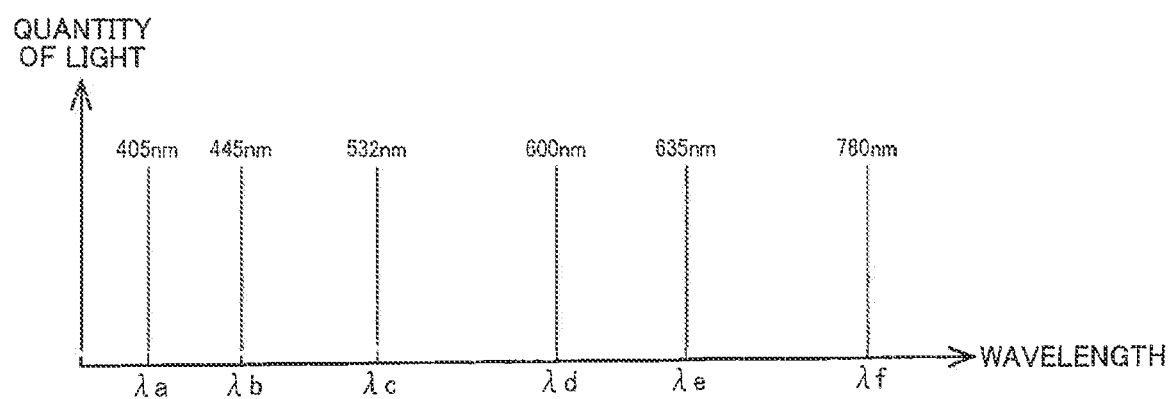
FIG. 7 is an example of laser light emitted by light sources in a second configuration example.

FIG. 7 is an example of the laser light emitted by the light sources LDa to LDf. The wavelengths of the laser light emitted by the light sources LDa to LDe are the same as those in FIG. 2. The light source LDf emits the infrared laser light having a wavelength λf=780 nm. The infrared laser light having the wavelength of 780 nm is used for fluorescence observation. For example, a fluorescent pigment of indocyanine green (ICG) absorbs the infrared light of around 780 nm and emits fluorescence of around 805 nm. The indocyanine green is used as an agent for fluorescence observation and is applied by splaying in a living body, an intravenous injection, or the like.

The image sensor included in the imaging unit 213 includes a pixel sensitive to the infrared light. That is, the image sensor includes the R pixel, G pixel, and B pixel, and the filter of the R pixel transmits the infrared light. As will be described later, the pixel sensitive to the infrared light and the light emission sequence may be implemented in various modified manners.

Figure 8:
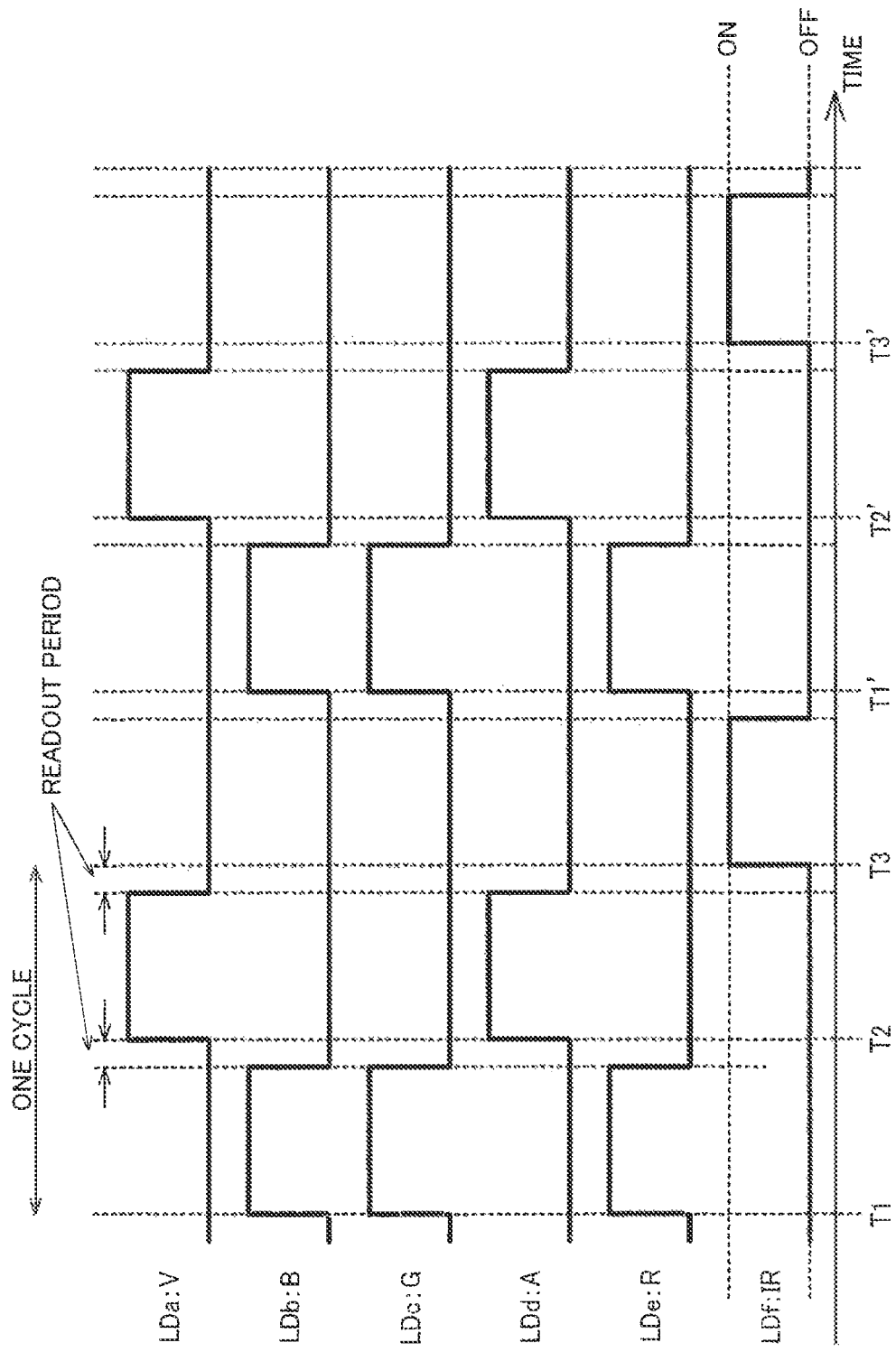
FIG. 8 is a light emission sequence of the illumination light in a second embodiment.

Next, operation of the endoscope apparatus 10 according to the second embodiment is described. FIG. 8 is the light emission sequence of the illumination light in the second embodiment. In FIG. 8, T1 and so on represent timings. A word "timing" is hereinafter abbreviated to T1 and so on.

As illustrated in FIG. 8, the image capturing operation is performed three times in one cycle from T1 to T1'. That is, one cycle includes three imaging frames. The illumination light control circuit 150 causes the light sources LDb, LDc, and LDe to emit light in a period from T1 to T2 excluding the readout period by the image sensor. The illumination light control circuit 150 causes the light sources LDa and LDd to emit light in a period from T2 to T3 excluding the readout period by the image sensor. The illumination light control circuit 150 causes the light source LDf to emit light in a period from T3 to T1' excluding the readout period by the image sensor. The illumination light control circuit 150 repeats the same light emission sequence thereafter. As a result, six images can be acquired approximately simultaneously. That is, the V image, B image, G image, A image, R image, and IR image can be acquired approximately simultaneously.

The first processing circuit 110 selects the IR image as the diagnosis support image and outputs the IR image to the diagnosis support section 121. The diagnosis support section 121 extracts the diagnosis support information based on the IR image. The diagnosis support information includes information about a fluorescence region by the ICG, a contour of the fluorescence region, brightness of fluorescence, or distribution of fluorescence. The diagnosis support information also includes information about contrast between the fluorescence region and an adjacent region. The diagnosis support information may include one or a combination of these types of information.

In the present embodiment, the diagnosis support section 121 extracts the diagnosis support information based only on the IR image, and does not use remaining five images. The diagnosis support information is extracted from the image different from the images combined to generate the display image in both the normal light observation mode and the NBI observation mode.

The first processing circuit 110 generates the display image using the V image, B image, G image, A image, and R image. Unlike the first embodiment, the white light image includes the V image in the second embodiment. The light quantity ratio of the laser light of V, B, G, A, and R is set to a white balance that generates a white light image as the display image.

The V image has characteristics to show a capillary in a surface layer with higher contrast compared with the contrast in the B image. Accordingly, the white light image according to the present embodiment shows the capillary in the surface layer with higher contrast compared with the contrast in the white light image based on four colors of B, G, A, and R in the first embodiment. The first processing circuit 110 combines the V image and the B image to set a resultant as a B channel of the display image, sets the G image as a G channel of the display image, and combines the A image and the R image to set a resultant as an R channel of the display image. Then, the first processing circuit 110 outputs the display image including the RGB channels described above to the display section 300.

The display section 300 may display an image including the white light image described above and the IR image superimposed on the white light image. For example, when the operator selects an IR superimposed image by the input section 600, the display section 300 displays the image including the white light image and the IR image superimposed thereon. As for a method for superimposing a fluorescence image, various common image superimposing technology can be used.

As a result, the operator can visually confirm the fluorescence image. In addition, the support display information based on the fluorescence image can be added to the display image. For example, the first processing circuit 110 receives the diagnosis support information from the second processing circuit 120, and adds the support display information to the display image based on the diagnosis support information. In this case, the support display information includes a boundary line of the fluorescence region, or a highly visible color superimposed on the fluorescence region, for example. The first processing circuit 110 superimposes this support display information on the display image.

The above describes an example where the image sensor including the RGB color filters is used, however, the image sensor may include the IR pixel in addition to the R pixel, G pixel, and B pixel, for example. An IR filter is disposed for the IR pixel. The IR filter hardly transmits the laser light of 780 nm, but transmits the light of around 805 nm. In this case, the infrared laser light is emitted with the violet laser light and the orange laser light. That is, the image capturing operation is performed twice in one cycle of the light emission sequence. The illumination light control circuit 150 causes the light sources LDb, LDc, and LDe to emit light in the period from T1 to T2 excluding the readout period by the image sensor. The illumination light control circuit 150 causes the light sources LDa, LDd, and LDf to emit light in the period from T2 to T1' excluding the readout period by the image sensor.

In the embodiment described above, m is four or more. The light source section 140 includes first light source, second light source, third light source, and sixth light source. The first light source emits first light which has a peak wavelength in a range from 436 to 480 nm. The second light source emits second light which has a peak wavelength in a range from 481 to 585 nm. The third light source emits third light which has a peak wavelength in a range from 616 to 700 nm. The sixth light source emits sixth light, and the sixth light has a peak wavelength in a range from 701 to 999 nm.

In FIGS. 6 and 8, the first light source corresponds to the light source LDb, the second light source to the light source LDc, the third light source to the light source LDe, and a sixth light source to the light source LDf According to the present embodiment, with the fourth light source that emits the infrared laser light, the fluorescence image of the object can be captured. The fluorescence image based on the agent of the ICG or the like can be captured. Then, the fluorescence image is input to the second processing circuit 120, so that the diagnosis support information can be extracted from the fluorescence image.

Furthermore, according to the present embodiment, the light source section 140 causes the first light source, second light source, and third light source to emit light in the first imaging frame, and the sixth light source in the second imaging frame. n is four or more. The display image group includes first to third images corresponding to the first to third light. The support image is a sixth image corresponding to the sixth light.

In FIG. 8, an imaging frame between T1' and T2' is the first imaging frame, and an imaging frame between T3 and T1' is the second imaging frame. In this case, the second imaging frame is before the first imaging frame. The second imaging frame may be after the first imaging frame. For example, in FIG. 8, the light source LDf may emit light between T2 and T3, and the light sources LDa and LDd may emit light between T3 and T1'.

According to the present embodiment, the support image to be input for the AI processing is the IR image. When only one image is input for the AI processing, a load of the AI processing becomes smaller compared with a load in a case where the diagnosis support information is extracted from a plurality of images.

4. Third Embodiment

Next, the third embodiment is described. The description that is common to that of the first and second embodiments is omitted.

The configuration of the endoscope apparatus 10 is the same as that illustrated in FIG. 1. Characteristics of the laser light emitted by the light sources LDa to LDe are as illustrated in FIG. 2. In the third embodiment, light emission by the light source LDc with the light quantity 2 is omitted from the light emission sequence in FIG. 5. That is, the image capturing operation is performed twice in one cycle from T1 to T1'. The illumination light control circuit 150 causes the light sources LDb, LDc, and LDe to emit light in the period from T1 to T2 excluding the readout period by the image sensor. The illumination light control circuit 150 causes the light sources LDa and LDd to emit light in the period from T2 to T1' excluding the readout period by the image sensor. The illumination light control circuit 150 repeats the same light emission sequence thereafter. As a result, five images can be acquired approximately simultaneously. That is, the V image, B image, G image with the light quantity 1, A image, and R image can be acquired approximately simultaneously.

The first processing circuit 110 outputs three images including the G image, A image, and R image to the diagnosis support section 121. A method for generating the display image in the normal light observation mode is the same as that in the first and second embodiments. In a red band imaging (RBI) observation mode, the first processing circuit 110 combines the G image, A image, and R image to generate an RBI image, and outputs the RBI image to the display section 300 as the display image. The RBI is a method for providing an image that facilitates visual recognition of a deep blood vessel or a bleeding point.

The diagnosis support section 121 extracts the diagnosis support information with each of the G image, A image, and R image as input for the AI processing. The G image, A image, and R image are combined to generate the display image of the RBI. However, the individual G image, A image, and R image, not a combined image, are input for the AI processing. The diagnosis support section 121 extracts the target portion from each of the G image, A image, and R image, for example. Alternatively, the diagnosis support section 121 may extract the target portion based on a comparison result between the A image and the R image.

The above describes an example where the first processing circuit 110 outputs the three images including the G image, A image, and R image to the diagnosis support section 121, however, the first processing circuit 110 may output two images including the A image and the R image to the diagnosis support section 121.

In the embodiment described above, m is four or more. The light source section 140 includes first light source, second light source, third light source, and fifth light source. The first light source emits first light which has a peak wavelength in a range from 436 to 480 nm. The second light source emits second light which has a peak wavelength in a range from 481 to 585 nm. The third light source emits third light which has a peak wavelength in a range from 586 to 615 nm. A fifth light source emits fifth light which has a peak wavelength in a range from 616 to 700 nm.

In the third embodiment, the first light source corresponds to the light source LDb, the second light source to the light source LDc, the third light source to the light source LDd, and the fifth light source to the light source LDe.

According to the present embodiment, with the third light source that emits the orange laser light, the RBI observation mode can be implemented together with the green laser light and the red laser light. In the RBI observation mode, the blood vessel in a deep part of the mucosa or the bleeding point in the mucosa can be observed with high contrast. Furthermore, the support image group includes the images captured with the orange laser light, green laser light, and red laser light, so that the diagnosis support information can be extracted from the images including the blood vessel in the deep part of the mucosa or the bleeding point in the mucosa with high contrast.

Furthermore, according to the present embodiment, the light source section 140 causes the first light source, second light source, and third light source to emit light in the first imaging frame, and the fifth light source in the second imaging frame. n is four or more. The first display image group includes first to third images corresponding to the first to third light. The second display image group includes the second and third images corresponding to the second and third light and a fourth image corresponding to fourth light. The support image group includes the third image and a fifth image. When the first display mode is set, the first processing circuit 110 combines the images in the first display image group to generate the first display image, and outputs the support image group to the second processing circuit 120. When the second display mode is set, the first processing circuit 110 combines the images in the second display image group to generate the second display image, and outputs the support image group to the second processing circuit 120.

In the third embodiment, the second display image group includes the G image, A image, and R image. The support image group is identical. The second display image is generated by combining these three images. On the other hand, these three images are separately input to the second processing circuit 120 as individual images. That is, the images in the support image group input to the second processing circuit 120 differ from the images in the second display image group.

5. Fourth Embodiment

Next, a fourth embodiment is described. The description that is common to that of the first to third embodiments is omitted.

In the fourth embodiment, images in respective observation modes are displayed later based on images recorded in observation. The images may be still images or a video.

Figure 9:
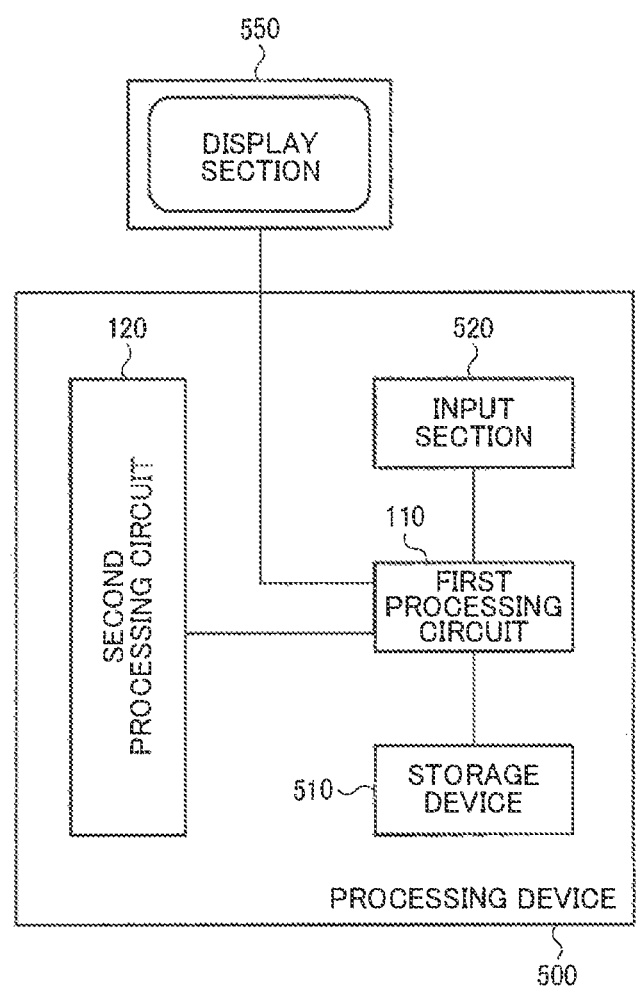
FIG. 9 is a configuration example of a processing device.

FIG. 9 is a configuration example of a processing device 500. The processing device 500 includes the first processing circuit 110, a storage device 510, and an input section 520. The processing device 500 may further include the second processing circuit 120. The processing device 500 is an information processing device such as a personal computer (PC), a tablet, or a server, for example. Alternatively, the processing device 500 is the control device 100 of the endoscope apparatus 10, for example. In this case, the storage device 510 is included in the control device 100, the input section 520 corresponds to the input section 600, and a display section 550 corresponds to the display section 300.

The storage device 510 stores images captured by the endoscope apparatus 10. For example, the storage device 510 stores the six images in the first embodiment, for example. That is, the storage device 510 stores the V image, B image, G image with the light quantity 1, G image with the light quantity 2, A image, and V image. When the processing device 500 is the PC, the images are forwarded from the endoscope apparatus 10 to the processing device 500 via a USB, a network, or the like, and are stored in the storage device 510. Alternatively, when the processing device 500 is the control device 100 of the endoscope apparatus 10, the images output from the first processing circuit 110 are stored in the storage device 510. The above describes an example where the images captured in the first embodiment are stored in the storage device 510, however, a configuration is not limited to this, and the images captured in the second or third embodiment may be stored in the storage device 510.

The operator selects the observation mode by the input section 520. For example, the processing device 500 causes the display section 550 to display options of the observation modes that can be generated from the images stored in the storage device 510. The operator selects a desired observation mode from the options by the input section 520. The input section 520 may be various operation devices such as a pointing device, a keyboard, or a button. Furthermore, when the processing device 500 is the control device 100 of the endoscope apparatus 10, the operator may select the observation mode by the operation section 220.

The first processing circuit 110 generates the display image based on the selected observation mode, and outputs the display image to the display section 550. When the storage device 510 stores the six images described above, any one of a first normal light observation mode, a second normal light observation mode, a third normal light observation mode, the NBI observation mode, and the RBI observation mode can be selected, for example. In the first normal light observation mode, the first processing circuit 110 generates the white light image by combining the B image, G image with the light quantity 1, A image, and R image. In the second normal light observation mode, the first processing circuit 110 generates the white light image by combining the V image, B image, G image with the light quantity 1, A image, and R image. In the third normal light observation mode, the first processing circuit 110 generates the white light image by combining the B image, G image with the light quantity 1, and R image. In the NBI observation mode, the first processing circuit 110 generates the NBI image by combining the V image and the G image with the light quantity 2. In the RBI observation mode, the first processing circuit 110 generates the RBI image by combining the G image with the light quantity 1, A image, and R image.

The operator may arbitrarily select a combination of images from the six images, and the first processing circuit 110 may generate the display image by combining the images in the combination.

When the processing device 500 is the information processing device, image processing software that can execute the same processing as the image processing performed by the endoscope apparatus 10 is installed to the information processing device, for example. Then, the first processing circuit 110 executes the image processing software to implement the image processing described above.

When the processing device 500 is the information processing device, the storage device 510 may be one of various storage devices such as a semiconductor memory, a hard disk drive, or an optical drive. Alternatively, image data may be input to the processing device 500 via an infrastructure such as a network, not from the storage device 510. For example, the endoscope apparatus 10 and the processing device 500 may be connected to the network, and the processing device 500 may acquire the image data from the endoscope apparatus 10 via the network.

When the processing device 500 includes the second processing circuit 120, the diagnosis support information can be further acquired. That is, the first processing circuit 110 outputs one or more images to be used to extract the diagnosis support information to the second processing circuit 120. The second processing circuit 120 performs the AI processing to the one or more images input from the first processing circuit 110 to extract the diagnosis support information, and outputs the diagnosis support information to the first processing circuit 110. The first processing circuit 110 adds the support display information to the display image based on the diagnosis support information, and outputs the resultant display image to the display section 550. A method for extracting the diagnosis support information is the same as that in the first to third embodiments.

In the embodiment described above, the processing device 500 includes the storage device 510 that stores first to n-th images (n is an integer of two or more), and the first processing circuit 110 that acquires the first to n-th images from the storage device 510. Each of the first to n-th images corresponds to any one of first to m-th light (m is an integer of two or more) with different colors. The first processing circuit 110 generates the display image based on the display image group including some images of the first to n-th images. The first processing circuit 110 generates the display image based on the display image group including some images of the first to n-th images, and outputs the support image different from the display image or the support image group not including the display image to the second processing circuit 120. Then, the first processing circuit 110 acquires the diagnosis support information. The diagnosis support information is output from the second processing circuit 120 based on the support image or the support image group.

According to the present embodiment, the observation image can be generated and displayed not only during a real-time examination by the endoscope apparatus 10, but also after the real-time examination. Furthermore, the image can be generated in a desired observation mode afterward regardless of the observation mode during the real-time examination. For example, the operator can examine a lesion part noticed afterward in detail, or another operator can observe a concerned part, noticed when checking the image, in a desired observation mode. Furthermore, when a lesion part is found later, the operator can go back in time to observe the part again in a desired observation mode. For example, when a lesion part is newly found, the operator can generate a special light image from data acquired in a last examination to check a condition. Furthermore, when the processing device 500 is the information processing device, the observation image can be generated and displayed without the endoscope apparatus 10. Furthermore, a plurality of observers can perform observation or screening at different places.

6. Fifth Embodiment

Next, a fifth embodiment is described. The description that is common to that of the first to fourth embodiments is omitted.

Figure 10:
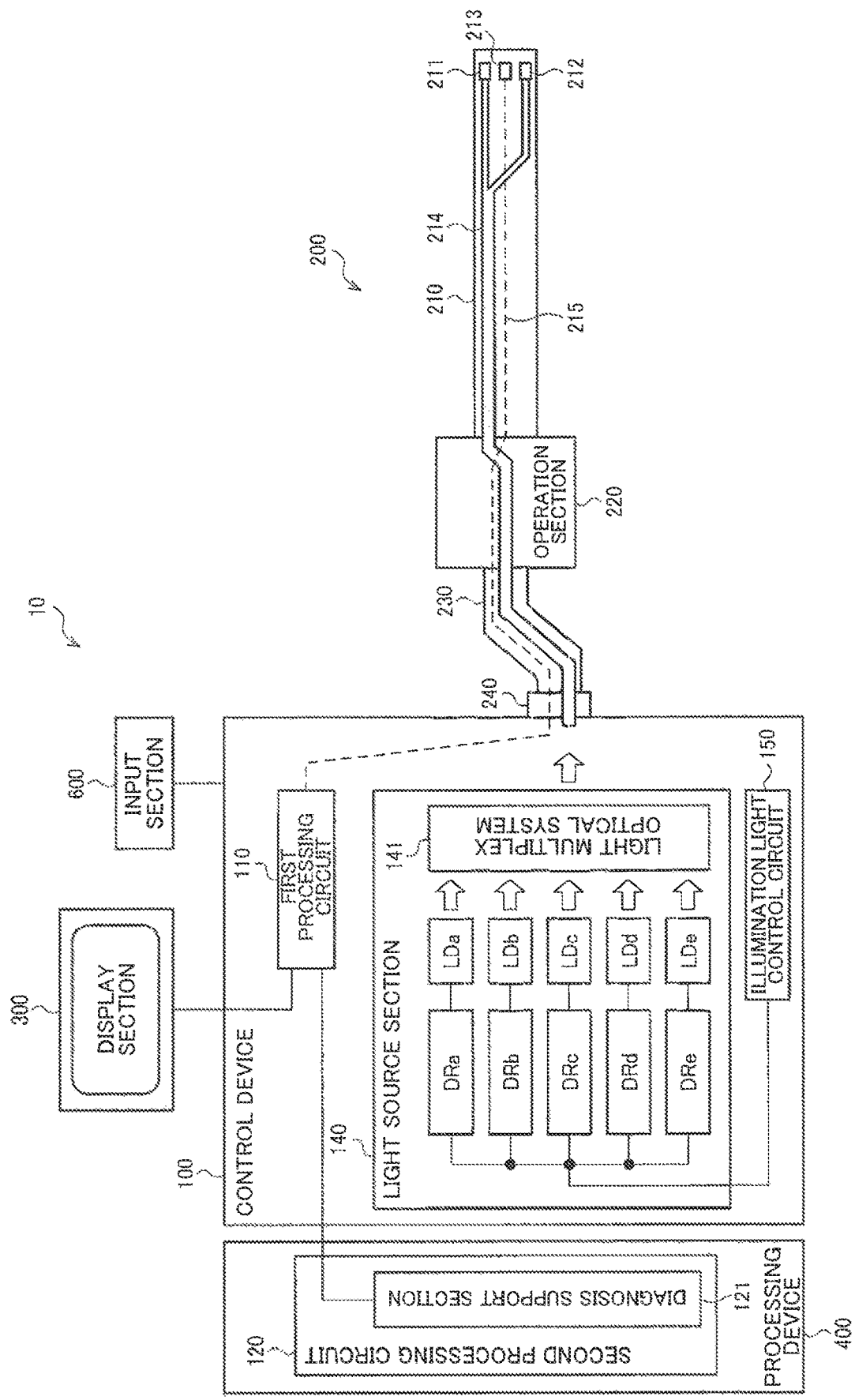
FIG. 10 is a configuration example of an endoscope system.

FIG. 10 is a configuration example of an endoscope system. The endoscope system includes the endoscope apparatus 10 and a processing device 400. In the fifth embodiment, the endoscope apparatus 10 does not include the second processing circuit 120, and the processing device 400 disposed separately from the endoscope apparatus 10 includes the second processing circuit 120. The processing device 400 is the information processing device such as a PC or a server, for example. The processing device 400 is not limited to a single information processing device, but may be a cloud processing system connected to a network, for example.

The control device 100 of the endoscope apparatus 10 includes an interface, not illustrated, used to communicate the images and the diagnosis support information. The interface may be one of various interfaces between devices. For example, the interface may be an interface for cable communication such as a USB or a LAN, or may be an interface for wireless communication such as a wireless LAN.

According to the first to fifth embodiments described above, the images are acquired approximately simultaneously, so that alignment between the different images is not required. However, the applicable target of the present disclosure is not limited to this. The alignment using common image recognition or image processing technology may be performed between a plurality of images, of course. Performing the alignment can provide the diagnosis support information including the position information more accurately.

Furthermore, the first to fifth embodiments are described with an example where the one or more images each captured in a single color are input to the second processing circuit 120. However, the applicable target of the present disclosure is not limited to this. Needless to say, the diagnosis support information may be extracted using an image generated by combining a plurality of images, such as the NBI image generated by combining the V image and the G image with the light quantity 2. At this time, an image selected by the operator is displayed as the display image. The first processing circuit 110 independently outputs one or more images most suitable for the diagnosis support to the diagnosis support section 121. As a result, the support information can be extracted using the one or more images most suitable for extraction of the support information. At the same time, operation, such as making a diagnosis, can be performed using the images most suitable for the operation. Furthermore, this configuration increases options for selecting the one or more images most suitable for extraction of the support information, and enables extraction of the diagnosis support information using images acquired by another endoscope system. At this time, the images used for the operation by the operator may happen to coincide with the images most suitable for the diagnosis support section 121. However, the effects of the present disclosure can be obtained by allowing these images to be independently selected and set.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
   an imaging device comprising an image sensor with blue, green, and red color filters, wherein the imaging device is configured to capture an image of an object;
   a light source device configured to emit a plurality of types of light with different colors as illumination light for the object;
   a first processing circuit configured to generate an image based on an image signal from the imaging device;
   a second processing circuit configured to generate diagnosis support information based on the image generated by the first processing circuit; and
   a control circuit,
   wherein the light source device is configured to emit:
     first light having a peak wavelength in a transmission wavelength band of the blue color filter;
     second light having a peak wavelength in a transmission wavelength band of the green color filter;
     third light having a peak wavelength in a transmission wavelength band of the red color filter;
     fourth light having a peak wavelength in the transmission wavelength band of the blue color filter; and
     fifth light having a peak wavelength in the transmission wavelength band of the red color filter,
   wherein the control circuit is configured to control the light source device to emit:
     the first light in a first imaging frame;
     the second light in either the first imaging frame or a second imaging frame different from the first imaging frame;
     the third light in the first imaging frame;
     the fourth light in the second imaging frame; and
     the fifth light in the second imaging frame,
   wherein the first processing circuit is configured to:
     generate a display image based on one of a first image group including images corresponding to the first light, the second light, the third light and the fifth light and a second image group including an image corresponding to the fourth light; and
     output a remaining one of the first image group and the second image group to the second processing circuit,
   wherein the second processing circuit is configured to generate diagnosis support information based on the remaining one of the first image group and the second image group output by the first processing circuit, and
   wherein the first processing circuit is configured to:
     perform image processing based on the diagnosis support information, to the display image; and
     output the display image after the image processing to a display.

2. The endoscope apparatus as defined in claim 1,
   wherein the light source device comprises:
     a first light source configured to emit the first light having the peak wavelength in a range from 436 to 480 nm;
     a second light source configured to emit the second light having the peak wavelength in a range from 481 to 585 nm;

a third light source configured to emit the third light having the peak wavelength in a range from 616 to 700 nm;

a fourth light source configured to emit the fourth light having the peak wavelength in a range from 400 to 435 nm; and a fifth light source configured to emit the fifth light having the peak wavelength in a range from 586 to 615 nm.

3. The endoscope apparatus as defined in claim 2, wherein the control circuit is configured to:

control the first to third light sources to emit the first to third lights in the first imaging frame; and control the fourth and fifth light sources to emit the fourth and fifth lights in the second imaging frame.

4. The endoscope apparatus as defined in claim 3, wherein:

a first image corresponds to the first light;
a second image corresponds to the second light;
a third image corresponds to the third light;
a fourth image corresponds to the fourth light;
a fifth image corresponds to the fifth light;
the first image group includes the first image, the second image, the third image, and the fifth image, and
the second image group includes the fourth image and the second image.

5. The endoscope apparatus as defined in claim 4, wherein:

the first processing circuit is configured to output the second image group to the second processing circuit as a support image group; and the second processing circuit is configured to generate the diagnosis support information based on the second image group.

6. The endoscope apparatus as defined in claim 5, wherein:

the diagnosis support information includes information about at least one of a position and contour of a target portion included in the object; and the first processing circuit is configured to:

perform the image processing of adding display information about the at least one of the position and contour of the target portion to the display image based on the diagnosis support information; and output a resultant display image applied with the image processing to the display.

7. The endoscope apparatus as defined in claim 4, wherein the control circuit is configured to control the second light source to emit light in the second imaging frame with a quantity of light different from a quantity of light of the second light source in the first imaging frame so as to emit sixth light.

8. The endoscope apparatus as defined in claim 7, wherein:

a sixth image corresponds to the sixth light; and
the first processing circuit is configured to generate a third image group including the fourth image and the sixth image.

9. The endoscope apparatus as defined in claim 8, wherein the first processing circuit is configured to output the second image group to the second processing circuit as a support image group, wherein, when a first display mode is set, the first processing circuit is configured to generate a first display image, as the display image, based on the first image group; and the second processing circuit is configured to generate the diagnosis support information based on the second image group, and wherein, when a second display mode is set, the first processing circuit is configured to generate a second display image based on the third image group;

the second processing circuit is configured to generate the diagnosis support information based on the second image group; and the first processing circuit is configured to:

perform the image processing, based on the diagnosis support information, to the second display image; and output the second display image after the image processing to the display.

* * * * *